US008142343B2

(12) United States Patent
Pickett et al.

(10) Patent No.: US 8,142,343 B2
(45) Date of Patent: *Mar. 27, 2012

(54) SUPRAPATELLAR EXTERNAL COUNTERPULSATION APPARATUS

(76) Inventors: David Anthony Pickett, Orrville, OH (US); James Russell Lusk, Costa Mesa, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/553,860

(22) Filed: Sep. 3, 2009

(65) Prior Publication Data

US 2010/0056850 A1 Mar. 4, 2010

Related U.S. Application Data

(63) Continuation of application No. 11/450,822, filed on Jun. 9, 2006, now Pat. No. 7,597,659, which is a continuation of application No. 10/881,079, filed on Jun. 30, 2004, now Pat. No. 7,074,177.

(51) Int. Cl.
*A61H 9/00* (2006.01)
*A61F 5/34* (2006.01)

(52) U.S. Cl. ........................................... 600/17; 600/16

(58) Field of Classification Search ..................... 600/16
See application file for complete search history.

(56) References Cited

U.S. PATENT DOCUMENTS

| | | | | |
|---|---|---|---|---|
| 2,361,242 A | | 10/1944 | Rosett | |
| 3,403,673 A | | 10/1968 | MacLeod | |
| 3,654,919 A | | 4/1972 | Birtwell | |
| 3,659,593 A | | 5/1972 | Vail | |
| 3,811,431 A | | 5/1974 | Apstein | |
| 3,859,989 A | | 1/1975 | Spielberg | |
| 3,862,629 A | | 1/1975 | Rotta | |
| 3,866,604 A | | 2/1975 | Curless et al. | |
| 4,091,804 A | | 5/1978 | Hasty | |
| 4,375,217 A | | 3/1983 | Arkans | |
| 4,753,226 A | * | 6/1988 | Zheng et al. | 601/150 |
| 5,109,832 A | | 5/1992 | Proctor et al. | |
| 5,554,103 A | | 9/1996 | Zheng et al. | |
| 5,571,075 A | * | 11/1996 | Bullard | 601/152 |
| 5,997,540 A | | 12/1999 | Zheng et al. | |
| 6,450,981 B1 | | 9/2002 | Shabty et al. | |
| 6,494,852 B1 | * | 12/2002 | Barak et al. | 601/151 |
| 6,572,621 B1 | | 6/2003 | Zheng et al. | |
| 6,589,267 B1 | | 7/2003 | Hui | |
| 6,620,116 B2 | | 9/2003 | Lewis | |
| 6,736,786 B1 | | 5/2004 | Shabty et al. | |
| 6,752,771 B2 | * | 6/2004 | Rothman et al. | 601/44 |
| 6,770,041 B2 | | 8/2004 | Rastegar et al. | |
| 7,074,177 B2 | * | 7/2006 | Pickett et al. | 600/17 |

(Continued)

OTHER PUBLICATIONS

Bonetti, et al., "Enhanced external counterpulsation improves endothelial function in patients with symptomatic coronary artery disease," *Journal of the American College of Cardiology*, vol. 41, No. 10 pp. 1761-1768, 2003.

(Continued)

*Primary Examiner* — Carl H. Layno
*Assistant Examiner* — Jon-Eric C. Morales
(74) *Attorney, Agent, or Firm* — Knobbe, Martens, Olson & Bear LLP

(57) ABSTRACT

An external counterpulsation apparatus has an efficient cuff and bladder system. Embodiments of this system generally allow effective treatment at lower pressures and a reduced total body surface area being compressed. An accurate and reliable combination of automatic and preset timing for inflation and deflation of the bladder system is used to simplify use of the apparatus.

20 Claims, 28 Drawing Sheets

U.S. PATENT DOCUMENTS

| | | | | |
|---|---|---|---|---|
| 7,597,659 | B2 | 10/2009 | Pickett et al. | |
| 2002/0099409 | A1 | 7/2002 | Hui | |
| 2002/0107461 | A1 | 8/2002 | Hui | |
| 2002/0169399 | A1 * | 11/2002 | Rastegar et al. | 601/49 |
| 2002/0173735 | A1 * | 11/2002 | Lewis | 601/149 |
| 2003/0050551 | A1 * | 3/2003 | Shabty et al. | 600/407 |
| 2003/0144690 | A1 * | 7/2003 | Zheng et al. | 606/201 |
| 2005/0075531 | A1 | 4/2005 | Loeb et al. | |
| 2006/0004245 | A1 * | 1/2006 | Pickett et al. | 600/16 |

OTHER PUBLICATIONS

Bonetti, et al., "Enhanced external counterpulsation for ischemic heart disease," *Journal of the American College of Cardiology*, vol. 41, No. 11, 00.1918-1925, 2003.

Lakshmi, et al., "Relation of the pattern of diastolic augmentation during a course of enhanced external counterpulsation (EECP) to clinical benefit (from the international EECP patient registry [IEPR])," *The American Journal of Cardiology*, vol. 89, pp. 1303-1305, Jun. 1, 2002.

Linnemeier. et al. "Enhanced external counterpulsation for the relief of angina in patients with diabetes: safety, efficacy and 1-year clinical outcomes," *American Heart. Journal*, vol. 146, No. 3, Sep. 2003.

Michaels, et al, "Left ventricular systolic unloading and augmentation of intracoronary pressure and Doppler flow during enhanced external counterpulsation," *American Heart Association Inc.*, pp. 1237-1242, Sep. 3, 2002.

Werner, et al, "Pneumatic External Counterpulsation: A new noninvasive method to improve organ perfusion, "*The American Journal of Cardiology*, vol. 84, pp. 950-952, Oct. 15, 1999.

Werner, et al, "Changes of cerebral blood flow velocities during enhanced external counterpulsation, "*Acta Neural Scand*, pp. 405-411 2003.

* cited by examiner

SUPRAPATELLAR EXTERNAL COUNTERPULSATION APPARATUS

RELATED APPLICATION INFORMATION

This application is a Continuation of U.S. patent application Ser. No. 11/450,822, filed Jun. 9, 2006, now U.S. Pat. No. 7,597,659, issued Oct. 6, 2009, which is a Continuation of U.S. patent application Ser. No. 10/881,079 filed Jun. 30, 2004, now U.S. Pat. No. 7,074,177, issued Jul. 11, 2006, each of which is incorporated in its entirety by reference herein.

BACKGROUND OF THE INVENTION

1. Field of the Invention

This invention relates generally to the field of external counterpulsation.

2. Background of the Invention

Cardiac disease remains a significant health problem in the United States and in the world. Although there are a variety of pharmacological and interventional therapies to treat cardiac disease, many patients are not adequately helped by traditional treatments. In particular, the impaired healths of many cardiac disease patients create a substantial risk of morbidity and mortality for interventional therapies such as coronary bypass surgery. Unsuitable coronary anatomy, prior revascularization attempts or other comorbid conditions may still preclude less-invasive therapies such as percutaneous transluminal coronary angioplasty. Thus, the development of non-invasive therapies may provide additional health benefits to patient populations that cannot tolerate or have gained limited benefits from traditional treatments.

External counterpulsation (ECP) is a technique that has demonstrated effectiveness in treating angina and congestive heart failure (CHF). ECP is an outgrowth of research from the 1950's directed at augmenting the low cardiac output of patients with advanced cardiac disease. External counterpulsation is a noninvasive procedure whereby cuffs are placed around the lower extremities of the body, inflated during the filling phase of the heart, and rapidly deflated during the contractile phase. During the filling or diastolic phase of the heart, the chambers of the heart are passively filled with venous blood before the next contraction. By rapidly inflating the cuffs during diastole, venous pressure is increased increased in the peripheral regions of the body and venous blood return to the heart is enhanced. This increased ventricular filling or preloading results in an increased ejection of blood from the ventricles during the next systolic phase, which can enhance the cardiac output. Increased arterial pressure during diastole may also enhance filling of the coronary arteries. The rapid deflation of the cuffs during the period of systole or contraction lowers the peripheral vascular resistance (PVR) which the heart pumps against and further enhances cardiac output. A reduction in PVR lessens the workload of an impaired heart by decreasing the effort used to maintain the forward flow of blood. To further enhance limb compression, portions of the limbs may be compressed sequentially from the distal limbs to the proximal limbs, rather than all portions simultaneously, to increase venous return of blood to the heart. The synchronization of inflation and deflation with the resting and contractile phases of the heart has been shown to increase blood flow to many vascular beds, including the coronary arteries. Furthermore, by increasing the diastolic pressure component of the mean perfusion pressure of the body tissues, the systolic pressure component used to maintain mean perfusion pressure may be reduced to further lower the workload of the heart. When external counterpulsation is performed, plethysmographic tracings of the blood pressure waveform will show a decrease in the systolic peak and an increase in the diastolic peak. A diastolic-to-systolic effectiveness ratio, calculated by dividing the peak diastolic amplitude by the peak systolic amplitude, is commonly used to measure the hemodynamic changes induced by external counterpulsation.

Interestingly, although the standard ECP treatment consists of thirty-five hours of treatment over seven weeks, the benefits of ECP persist beyond the thirty-five hours during which ECP is applied to a patient and may benefit more than just the cardiovascular system. It has been hypothesized that the limited duration of enhanced blood flow may increase the shear stress in the endothelial walls of the vasculature. Shear stress is considered a major stimulus for angiogenesis and may upregulate the production of growth factors such as Vascular Endothelial Growth Factor and Hepatocyte Growth Factor. This shear stress also increases endothelial release of nitric oxide, which may have vasodilatory, anti-platelet, anti-thrombotic, anti-proliferative and anti-inflammatory effects on the vasculature. Research also suggests that nitric oxide may have beneficial antioxidant effects.

SUMMARY OF THE INVENTION

One embodiment of the invention is an external counterpulsation system that advantageously employs smaller balloons and cuffs applied to limited areas of the body to produce counterpulsation. With smaller balloons, lower inflation pressures can be used in the device because high pressures are not needed to provide high airflow rates for inflation and deflation of smaller balloons. A smaller cuff and balloon size also allows for better fitting of the device to the patient. An improved fit increases the degree of compression in body areas and provides a greater yield of blood flow for the limited compression area.

By using lower pressures to perform the external counterpulsation, the ECP system has no need to prematurely decompress the balloons during a premature ventricular contraction (PVC). Premature decompression is not required because the PVC is no longer contracting against high inflation pressures that result in a higher workload for the heart.

One embodiment of the invention comprises a plurality of inflatable bladders and cuffs, where each bladder has a surface area of about forty square inches for compressing the body of the patient. The bladders are held against a patient's body by cuffs that have a width of about six inches. The superior-posterior knee regions, the inguinal regions and the buttocks are the preferred areas of compression. Compression of remaining portions of the legs and pelvic region are not required. The bladders are inflated by an air compressor that is limited by a pressure regulator to pressurizing the bladders to a maximum of about 160 mm Hg to about 220 mm Hg. Inflation of the bladders is controlled by valves that open and close to inflate and deflate the balloons. These valves may be integrated into a table used to treat the patient. In turn, the valves are controlled by a valve controller that generates control signals based upon the ECG signal received from the patient. In one embodiment of the invention, an external ECG monitor attached to the patient provides the ECG signal used to generate the control signals. The ECG output from the external ECG monitor is attached to the ECP system through an ECG input connector that accepts ECG output from any of a variety of external ECG monitors. Alternatively, the ECP system has an integrated ECG monitor that is attachable to the patient to provide an ECG signal.

The ECG output is received by the ECP system and the signal is squared to amplify the signal and to make the signal deflections positive. This squared ECG signal is sent to a programmable logic controller (PLC) that identifies the peaks in the squared ECG signal and generates valve control signals coordinated to the timing of the peaks. In one embodiment of the invention, a first control signal is initiated about 280 milliseconds following the detection of a peaked signal and is transmitted to the valve controlling the inflation of the lower thighs. Forty milliseconds after the first control signal, a second control signal is sent to a valve controlling the upper thighs and forty milliseconds after the second control signal, a third control signal is sent to the valves controlling the buttocks. The three control signals stop about 370 milliseconds after the initiation of the third control signal. Alternatively, the timing of the first control signal may be calculated based upon the duration of the contractile cycle of the heart, which is inversely related to the heart rate. In this alternative embodiment, the delay interval before first control signal shortens as the heart rate increases, thereby allowing treatment of patients with higher baseline heart rates.

In one embodiment of the invention, the ECP system continues to generate control signals independent of whether an ECG signal is detected during the control signal cycle. Thus, the ECP system will maintain inflation during a premature ventricular contraction. The ECP system does not have to prematurely deflate because the lower pressures used for ECP do not impose a significant increase in workload to the heart. Alternatively, the valve controller can cancel the control signal cycle upon detecting a signal and restart the control signal cycle with the newly detected signal.

In one embodiment, the valves that control bladder inflation are air assist pilot valves that are actuated from an air compressor that is separate from the air compressor providing pressure to the bladders. Use of two separate air compressors to provide pressure for two different purposes allows efficient selection and adjustment of each air compressor for each purpose and minimizes the total heat, pressure and noise generated.

The cuffs used in the lower pressure ECP system have several features that facilitate use of the cuffs for ECP. The cuffs have a buckle roller to promote tightening of the cuffs when attaching the cuffs to the patient. The cuffs also have a buckle shield to prevent pinching of the patient's skin during cuff tightening. The bladders may be reversibly attached to the cuff to allow changes in cuff materials in consideration of the skin ailments that the patient may have. Alternatively, the bladders may be formed by a portion of the cuff material adhered to a single piece balloon material. This alternate cuff is cheaper to manufacture and can be advantageously used as a disposable cuff.

Further embodiments of the invention have wheels and handles so that the system can be easily moved. Other embodiments may also have a pressure source connector for connecting an external source of pressurized air to the ECP system so that the air compressors in ECP system can be shut off or even eliminated from some embodiments of the invention. External sources of compressed air are provided through an outlet in the walls of some clinics or hospitals. In further embodiments, air valves are integrated within a single unit of the ECP system so that a patient lying on any surface can be treated by the system and the patient does not need to lie down on a table specifically designed for ECP.

One method of using the ECP system comprises attaching the cuffs and bladders of an ECP system to the upper-posterior portions of the knee, the inguinal areas and the buttocks of the patient. The chest leads of an external ECG monitor are connected to the patient and the ECG signal output of the ECG monitor is connected the ECP system. The ECP system is turned on and a treatment duration is set. The programmable logic controller begins detecting signal peaks in the squared ECG signal. In one embodiment of the invention, the programmable logic controller initiates a first control signals about 280 milliseconds after detecting a signal peak. The first control signal is sent to the valve that controls pressurization of the bladders compressing the upper posterior knees. This first control signal is followed about forty milliseconds later by a second control signal transmitted to a valve controlling the bladders that compress the inguinal regions. After about another forty milliseconds, a third control signal is sent to the valve pressurizing a third set of bladders that compress the buttocks. After about 370 milliseconds from the start of the third control signal, all three signals are terminated and the bladders are deflated. The programmable logic controller repeats the cycle until the treatment period ends. Alternatively, the first control signal can be initiated after a variable delay interval based upon the duration of average of the last eight contractile cycles of the patient.

Further features and advantages of the present invention will become apparent to those of skill in the art in view of the disclosure herein, when considered together with the attached drawings and claims.

BRIEF DESCRIPTION OF THE DRAWINGS

The structure and operation of the invention will be better understood with the following detailed description of embodiments of the invention, along with the accompanying illustrations, in which.

DETAILED DESCRIPTION OF THE PREFERRED EMBODIMENT

Figure 1B:
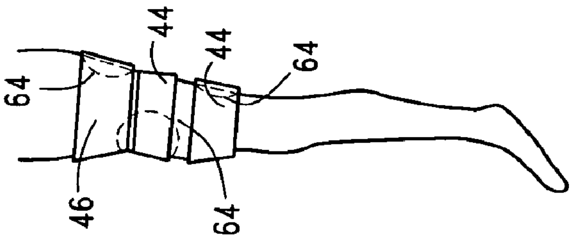
FIG. 1B is a side view of the left leg from FIG. 1A.

Despite the availability of ECP systems for several years and its reimbursable status under Medicare and health insurance plans, use of ECP has been hindered by several limitations in the existing technologies and the methods used to perform ECP. Existing ECP systems are large, noisy and complicated to operate. The air pressures used to inflate the existing systems are high and can cause discomfort or even pain to the limbs of patients undergoing treatments. The high pressures also cause the air in the ECP system to heat up, further adding to patient discomfort. The high pressures also cause a rapid jerking of patients' limbs during inflation, as well as a repetitive chaffing that can worsen skin conditions and cause musculoskeletal pains. Patient discomfort may result in noncompliance with the treatment and discontinuation of ECP before the conclusion of the standard seven-week treatment.

Existing ECP machines require high inflation pressures for several reasons. These machines use large inflation bladders placed against a large surface area of the limbs to attempt the greatest degree of limb compression. Larger bladders require higher volumes and higher pressures of air to obtain adequate airflow rates and limb compression. The high pressures can cause excessive skin irritation that an operator may attempt to alleviate by providing padding between the patient and the bladder. This additional protective padding in turn requires even higher pressures in the ECP system to provide sufficient compression of the limbs. The larger bladders of existing ECP systems also require larger air fill lines to provide satisfactory inflation and deflation airflow rates. Large air fill lines are additional air reservoirs that necessitate increased fluid volumes and pressures to operate the system and increase the noise and heat generated.

Another consequence of the high pressures in existing ECP systems is the required detection of premature ventricular contractions and the subsequent premature deflation of the ECP machine. A premature ventricular contraction (PVC) is an abnormal heartbeat that occurs earlier than expected when compared to regular heart activity. During an ECP treatment, a PVC causes the heart to pump against a high peripheral vascular resistance or afterload created by inflation of the ECP system. This severely increases the workload of the heart so much that existing ECP systems avoid compression during PVC's by detecting PVC's and prematurely deflating the bladders. A typical ECP patient, however, has advanced heart disease with an increased frequency of PVC's in their heart rhythms. In patients with frequent PVC's, the efficacy of ECP is reduced by frequent deflation caused by frequently detected PVC's.

The high cost of existing ECP systems has also limited the availability of these systems. Existing ECP systems have built-in electrocardiogram (ECG) modules for providing a synchronization signal to the system and built-in plethysmographs for monitoring the pulse waveform. Treatment centers, however, likely have pre-existing stand-alone ECG monitors that can provide the synchronization signal. Using a stand-alone ECG monitor would allow the operator to use a machine that he or she is already familiar with using and provides a synchronization signal that is updateable as the stand-alone ECG monitor is replaced. Likewise, treatment centers already have stand-alone plethysmograph devices, but the waveform information provided by plethysmographs is not needed if the operating parameters of the ECP machine are not derived from the waveforms.

Existing ECP systems are also complicated to operate. Existing ECP systems require the operator to take several steps and make several decisions before the initiation of an ECP treatment. These ECP systems require the operator to set several timing intervals on the machine, including the delay interval between a heartbeat and the onset of bladder inflation and the duration of the inflation. Operators also have to set the bladder inflation pressure. Setting all these parameters may delay the start of a treatment session and can make a treatment session less efficient or effective if the operator sets the wrong parameters on the machine.

Use of existing ECP systems is also made difficult by the numerous cuffs and air lines that must be connected to operate the system. Errors in connecting cuffs to the air lines or attaching cuffs to the limbs may delay the start of the treatment session and reduce the effectiveness of treatment. High pressure ECP systems also require cuffs designed to handle high bladder inflation pressures. These cuffs are not designed for patient comfort or ease-of-use by the operator. Because cuffs designed for high inflation pressures are also expensive to manufacture, the same set of cuffs have to be used by several patients in order to lower the usage cost of an ECP system.

Figure 1A:
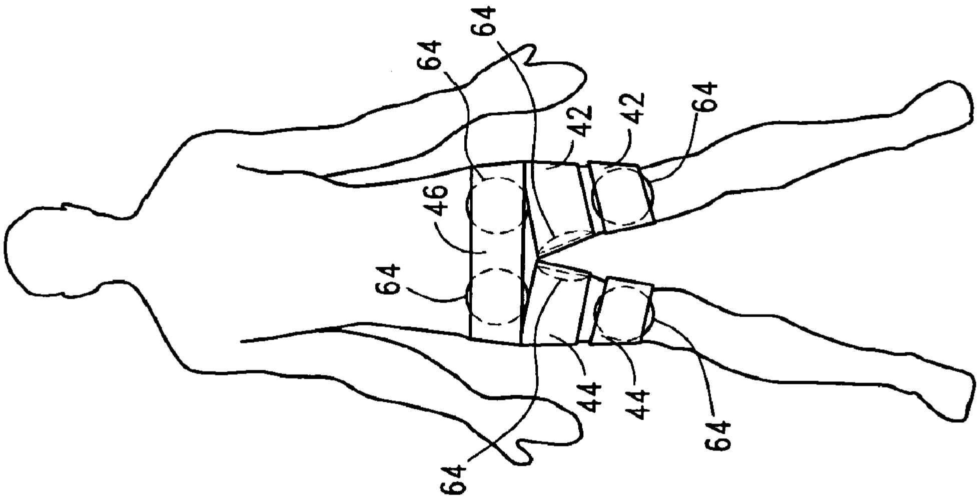
FIG. 1A is a posterior view showing one embodiment of the invention placed against the preferred compression areas of the body.

To address these limitations in existing ECP systems, one embodiment of the invention contemplated is an ECP system comprising small bladders that inflate at lower pressures and where the bladders are positioned at limited sites of the body but still produce effective circulatory augmentation despite the smaller body surface area compressed. By using smaller bladders with smaller cuffs, effective compression of these sites is increased because the smaller sizes allow deeper and more tightly fitted contact of these body areas. Also, because of anatomical narrowing or creasing, some anatomical sites are not effectively reached by large bladders fastened to large cuffs. The term "contact", as used herein, shall be given its ordinary meaning and shall also include the ability to transmit force to a patient through other layers or media, if any, between a bladder and a patient. Advantageous areas to compress with a smaller cuff and bladder system include the superior-posterior knee and inguinal regions of the body. The compressibility of the femoral vein, the principal deep vein trunk in the leg, is greatest at these two sites, but the use of this invention is not limited to this particular purpose or rationale. FIGS. 1A and 1B represent one embodiment of the invention with inflatable bladders 64 and cuffs 42, 44, 46 placed against the preferred compression sites at the superior-posterior knee regions, the inguinal regions and the buttocks. The bladders 64 and cuffs 42, 44, 46 are described in greater detail below. In this embodiment, six bladders 64, each having approximately thirty-six square inches of compression area, are used to compress the preferred body areas. Additional body areas may also be compressed, but are not necessary to achieve effective counterpulsation. Furthermore, increasing the body surface area compressed may increase the air volumes used and therefore increase patient discomfort and increase the generation of noise and heat. It is contemplated that existing ECP systems using a plurality of bladders for compressing the lower limb could be modified to have the capability of selectively inactivating a number of bladders during the treatment of a patient such that the remaining active bladders are located at the preferred compression sites and the effective total surface area of the remaining active bladders used to compress the body is limited to about 240 square inches or less.

By developing an ECP system employing lower inflation volumes, not only can lower pressures be used, but the timing of the inflation and deflation cycles can be simplified. Timing intervals become easier to maintain because there is less need to move large volumes of compressed air in and out of the bladders in a short time interval. This allows the duration of bladder inflation and the delay intervals between sequential inflation of the bladders to be preset in a low-volume ECP system.

Another benefit of an ECP system using lower volumes and pressures is that bladder deflation during PVC's is unnecessary. With an inflation pressure of about 160 mm Hg to about 220 mm Hg, an ECP system does not need to deflate the bladders when a PVC occurs because the heart is not longer contracting against a supra-physiological blood pressure. Furthermore, the ECP system is simplified because there is no need to differentiate between a sinus beats from PVC's. More importantly, a low-pressure ECP system eliminates the inefficiency of the ECP session caused by excessive deflation from detected PVC's.

In addition to angina and congestive heart failure, other uses for an ECP system may include but are not limited to adult and pediatric congenital heart disorders, pregnancy-related heart failure, ischemic bowel disease, peripheral vascular disease including carotid insufficiency and skin ulceration, Alzheimer's, cerebrovascular accidents, dementia, acute renal failure, chronic renal insufficiency and failure, liver disease, weight loss, alopecia, limb ischemia, sepsis and shock. Those skilled in the art are familiar with other conditions that may benefit from use of ECP.

Figure 2:
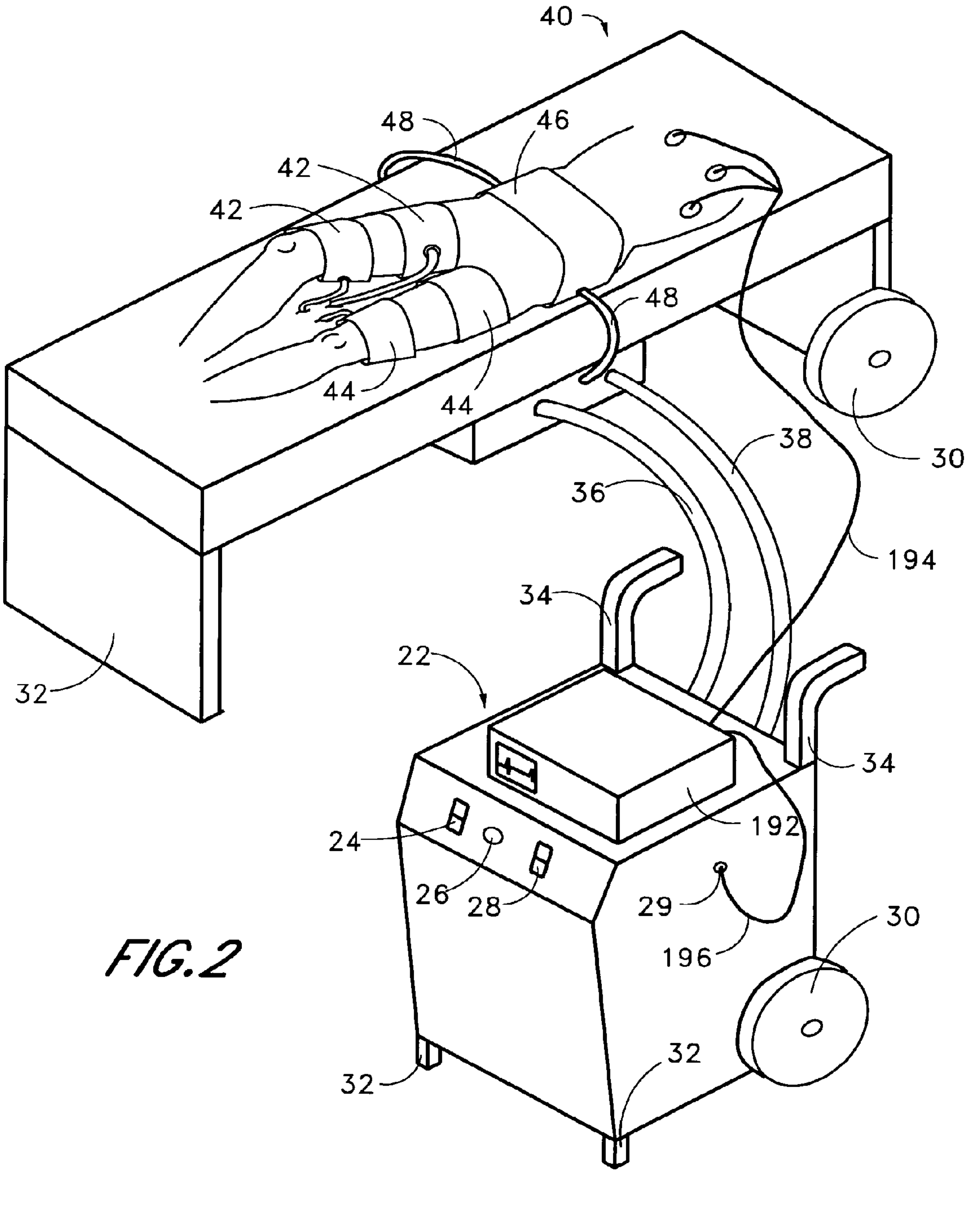
FIG. 2 shows one embodiment of the invention with an ECP system connected to a patient.
Figure 3:
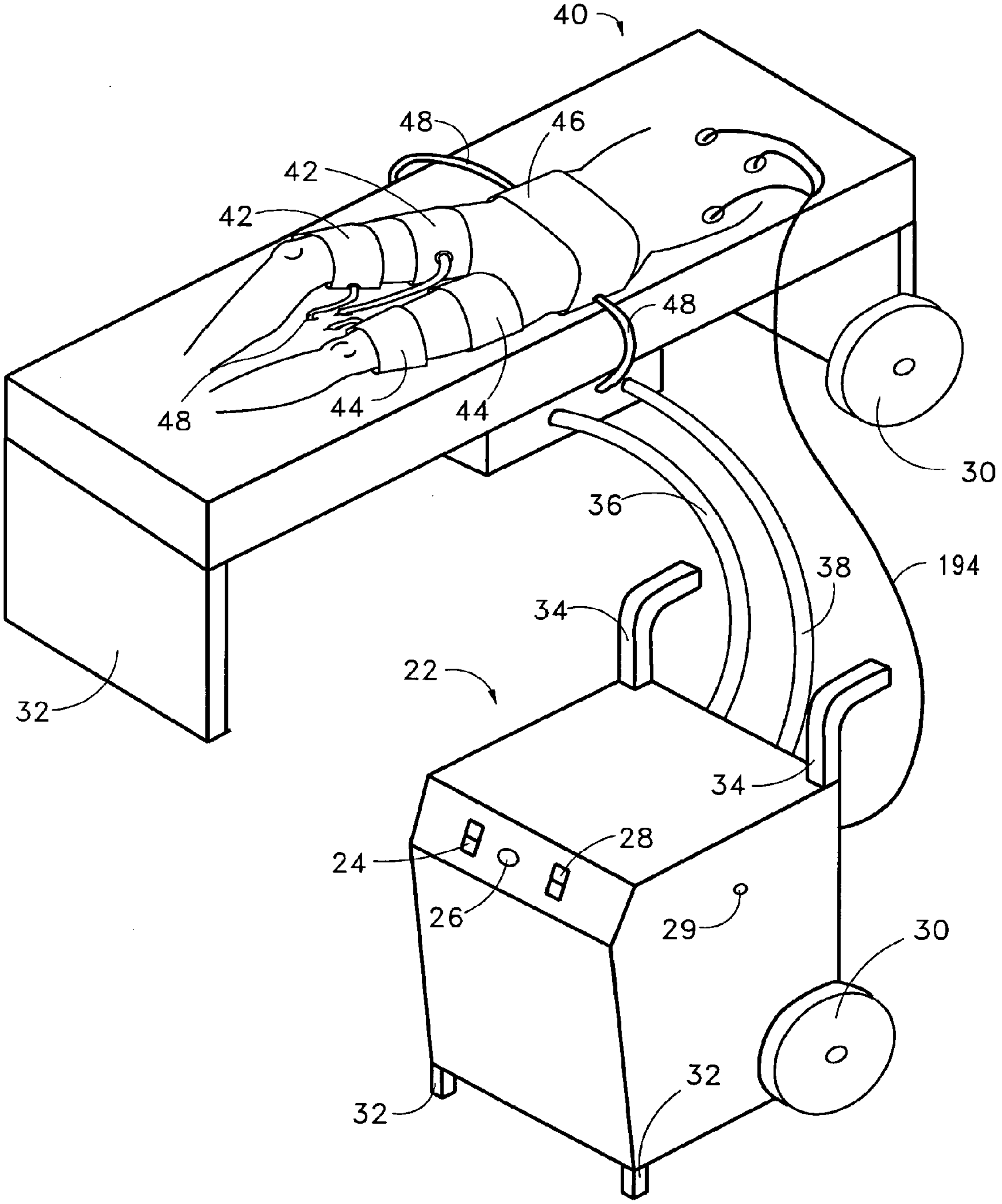
FIG. 3 shows one embodiment of the invention with an ECP system and integrated ECG monitor connected to a patient.

FIG. 2 shows one embodiment of the invention comprising an ECP system 22 and a table 40. ECP system 22 comprises a pressurized air system, a controller and a plurality of bladders attached to cuffs 42, 44 and 46. The controller comprises an ECG signal connector 29 that accepts an ECG signal from an external ECG signal source 192 and an ECG signal processor to generate at least one control signal from the ECG signal. An external ECG signal connector 29 allows a patient to undergo ECP treatment concurrently with any ongoing ECG monitoring being performed on the patient without attaching a duplicate set of chest leads to the patient. This is useful in an Intensive Care Unit (ICU) setting where a patient is already connected to an ECG monitor. One embodiment of ECG signal processor is described in further detail below. FIG. 3 shows another embodiment of the invention where an ECG monitor is integrated into the ECP system 22 and unprocessed ECG chest lead signals are provided to the ECG monitor by chest leads attached to the patient. The chest signal is processed by the ECG monitor and relayed to the ECG signal processor to generate the control signal. An ECG monitor output is optionally provided in this embodiment for providing ECG output to the telemetry monitors available in some hospital wards.

The control signal is transmitted through a control line 38 to table 40 for controlling the opening and closing of air valves that inflate and deflate the bladders. Pressurized air from ECP system 22 is transmitted to table 40 by a air line 36. From table 40 the air is directed to the air valves which distribute the pressurized air using bladder air lines 48 to the right leg cuffs 42, left leg cuffs 44 and buttock cuffs 46 that hold inflatable bladders. The controller may optionally have an on/off power switch 24 to control power to the ECP system 22 and/or a timer switch 26 that sets the treatment time.

Figure 4:
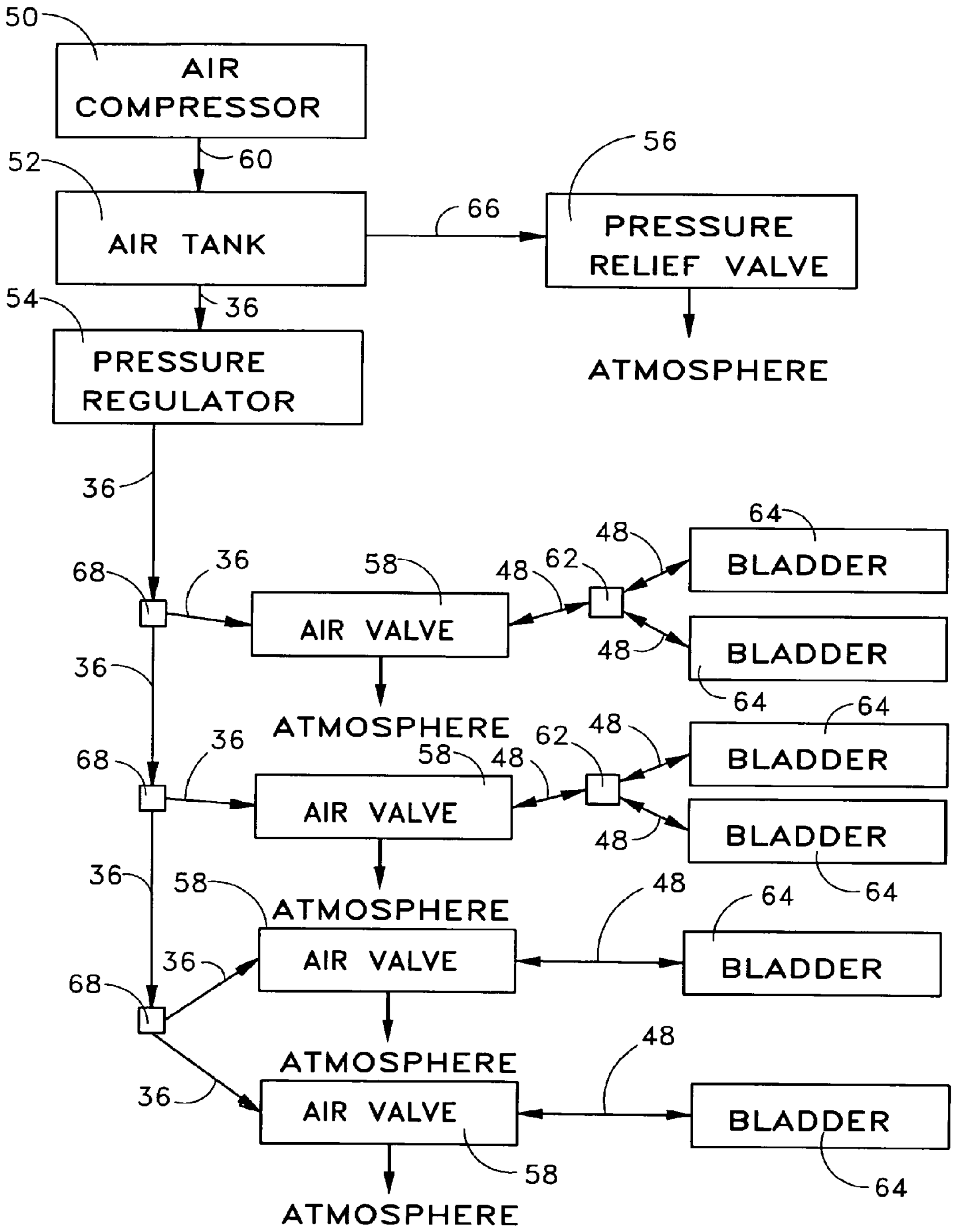
FIG. 4 depicts a schematic of one embodiment of the invention comprising a compressed fluid system that supplies fluid to the bladders.

One embodiment of the pressurized air subsystem is depicted schematically in FIG. 4. Pressurized air is supplied by an air compressor 50 which is capable of providing pressurized air to an air tank 52 through a compressor air line 60. Air compressor 50 is capable of a total free air output of about four to about eight cubic feet per minute (cfm) at a pressure of about four pounds per square inch (psi). Compressor air line 60 comprises a flexible hose having an internal diameter of about ½ inch to about ¾ inch. Air tank 52 has a capacity of about five gallons and is capable of withstanding an operating pressure of about 100 psi. Output from air tank 52 travels through air line 36 which comprises a flexible hose with an internal diameter of about one inch. Air line 36 connects to a pressure regulator 54. Air tank 52 also connects to a pressure relief valve 56 by a pressure relief valve fitting 66. Pressure relief valve 56 may be set to any pressure from about one psi to about five psi and vent about eight cfm or more of air. Pressure regulator 54 may be set to an output pressure of about three to about five psi and feed at least one air valve 58 through air line 36. Pressure from air line 36 may be distributed to a plurality of air valves 58 by air line tees 68 or any other kind of pressure distributor having multiple openings. Air valves 58 are connected to bladders 64 on the right leg cuffs 42, left leg cuffs 44 and buttock cuff 46 by bladder lines 48. Bladder lines 48 comprise ½ inch internal diameter flexible hose. In one embodiment of the invention, air valves 58 are ½ inch, 24-volt, normally closed, two-position, three-way, air pilot assist valves having an open and a closed configuration. In another embodiment, non-pilot air valves are used. In the closed configuration, air valves 58 prevent flow from air tank 52 to bladders 64. When closed, bladders 64 also vent to the atmosphere. In the open configuration, air valves 58 allow air pressure from air tank 52 to pressurize bladders 64 and prevent any venting. Ridged threaded barbs and hose clamps secure hoses 36, 48, 60 and 66 to the other components of the ECP system. One of skill in the art will understand that any of a variety of other mechanical fittings suitable for securing hoses may be used.

Figure 5:
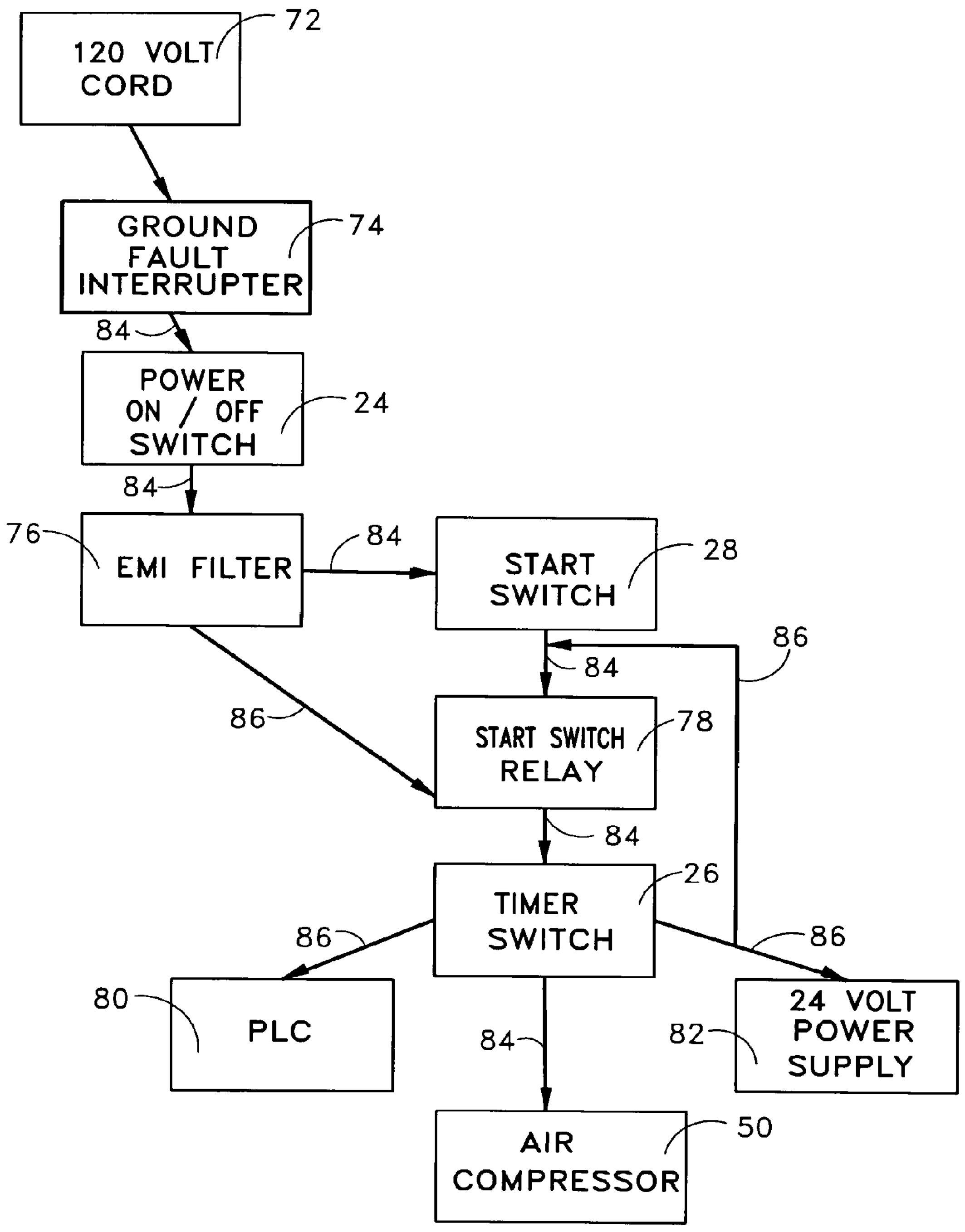
FIG. 5 illustrates a schematic of one embodiment of the invention comprising a 120-volt electrical system to power the ECP system.

One embodiment of an electrical power system for the ECP system is shown in FIG. 5. A 120-volt system is described below, but one skilled in the art will understand how to adapt the ECP system for use in a 110-volt, 220-volt, 240-volt or other system. A 120-volt power cord 72 feeds power to a re-settable ground fault interrupter (GFI) 74, which in turn connects to on/off power switch 24. In one embodiment, power switch 24 is a two-position double-pole lighted switch. Power switch 24 connects to an EMI filter 76 that in turn connects to a start switch 28 and a start switch relay 78 having an engaged and disengaged position. Start switch 28 is a momentary lighted single pole switch used to start ECP system 22. Start switch relay 78 also connects to start switch 28. When start switch 28 is in the engaged position, start switch 28 is capable of sending power to timer switch 26. Timer switch 26 has an active state and an inactive state. Timer switch 26 will go from the active state to the inactive state after a user-settable period. The power output from timer switch 26 is looped back to the output of start switch 28 to keep start switch relay 78 in the engaged position so long as timer switch 26 is in the active state. When timer switch 26 is in the active state, timer switch 26 provides power to air compressor 50, a programmable logic controller (PLC) 80 and a 24-volt power supply 82. In one embodiment, timer switch 26 can be set from about zero minutes to about sixty minutes. In another embodiment, the timer switch 26 can be set for any period of time. In one embodiment, the timer switch 26 does not reset upon loss of power. Wire 84 provides power to air compressor 50 from GFI 74 through timer switch 26. Typically, wire 84 comprises 14-gauge wire, but one skilled in the art will understand that other wire gauges may be used. Wires 86 provide power to start switch 28, programmable logic controller (PLC) 80 and 24-volt power supply 82. Wires 86 typically comprise 18-gauge wires, but those skilled in the art will understand that other wire gauges may be used. In one embodiment, PLC 80 is a 120-volt unit with at least one input and at least three outputs. The inputs range generally from about twelve volts to about twenty-four volts. The outputs range generally from about twelve volts to about twenty-four volts.

Figure 6:
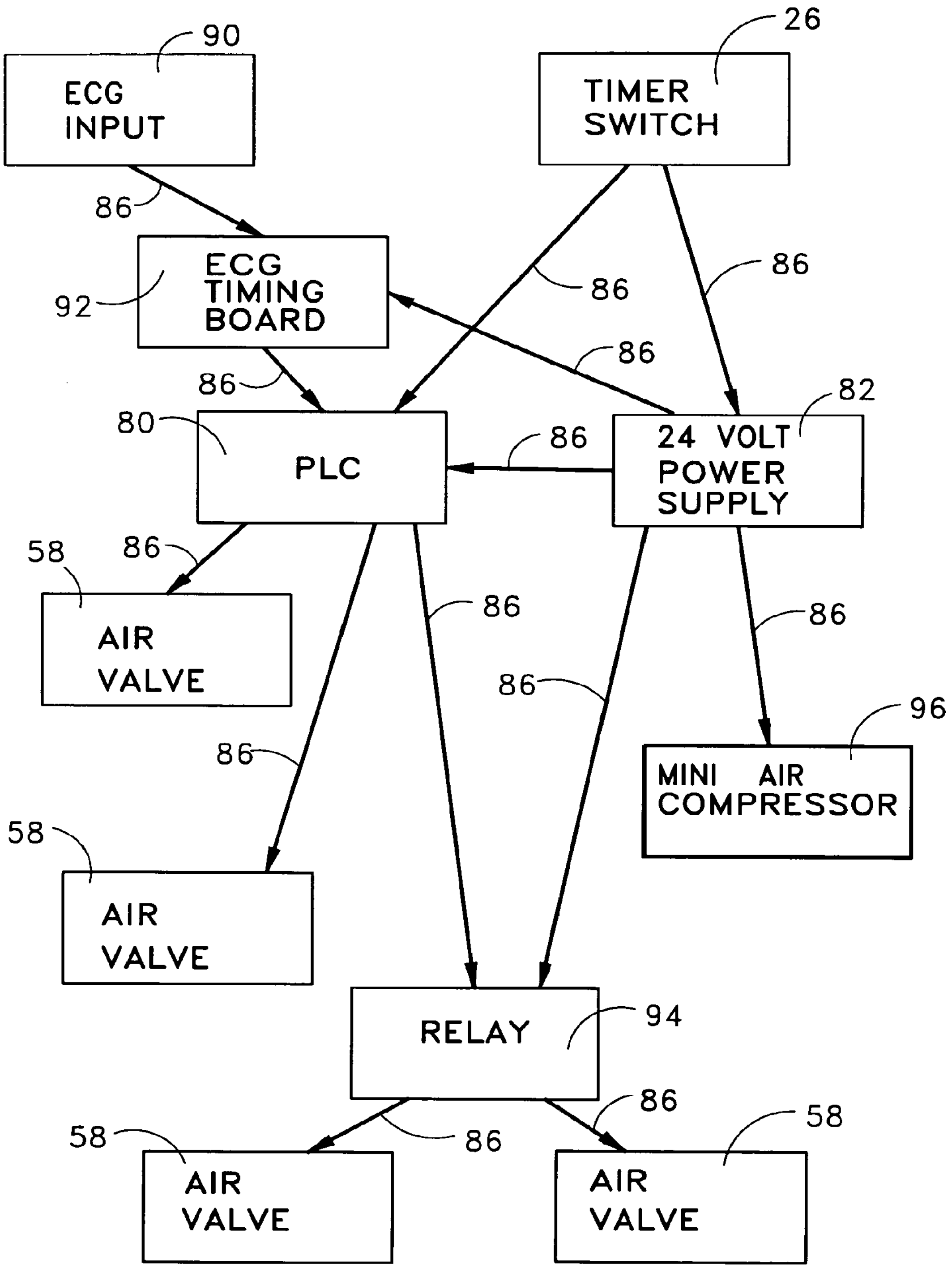
FIG. 6 represents a schematic of one embodiment of a 24-volt electrical system that powers some components of the ECP system.

FIG. 6 illustrates one embodiment of the external ECG input 90 and a 24-volt system used to power ECG system 22. Although a 24-volt system is described herein, one skilled in the art will know that the system can be adapted to voltages from about 6-volts to about 30-volts. A 24-volt power supply 82 supplies power to PLC 80, an ECG timing board 92, a PLC-to-air valve relay 94 and a mini-air compressor 96. ECG timing board 92 is a relay board that amplifies and relays the signal from external ECG input 90 to PLC 80. PLC 80 uses the amplified ECG signal from timing board 92 to output control signals to air valves 58 and PLC-to-air valve relay 94. In one embodiment, the outputs are generally spaced about forty milliseconds apart after the first output. In another embodiment, the outputs are generally spaced about 10 milliseconds to about 100 milliseconds apart. A first output or control signal regulates air valve 58 connected to bladders contacting the upper posterior knee or lower thigh. A second output regulates air valve 58 connected to bladders contacting the upper thigh or inguinal areas. A third output goes to PLC-to-air valve relay 94, which passes the third output to air valves 58 controlling compression of the buttocks. Wires 86 used for the 24-volt system are typically 18-gauge wires.

Figure 7:
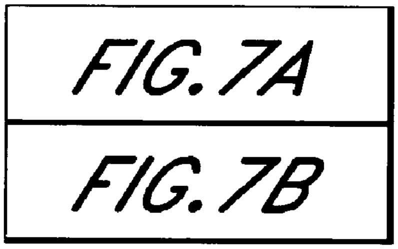
FIGS. 7A and 7B shows a schematic of one embodiment of the invention comprising the programming of the programmable logic controller.
Figure 7A:
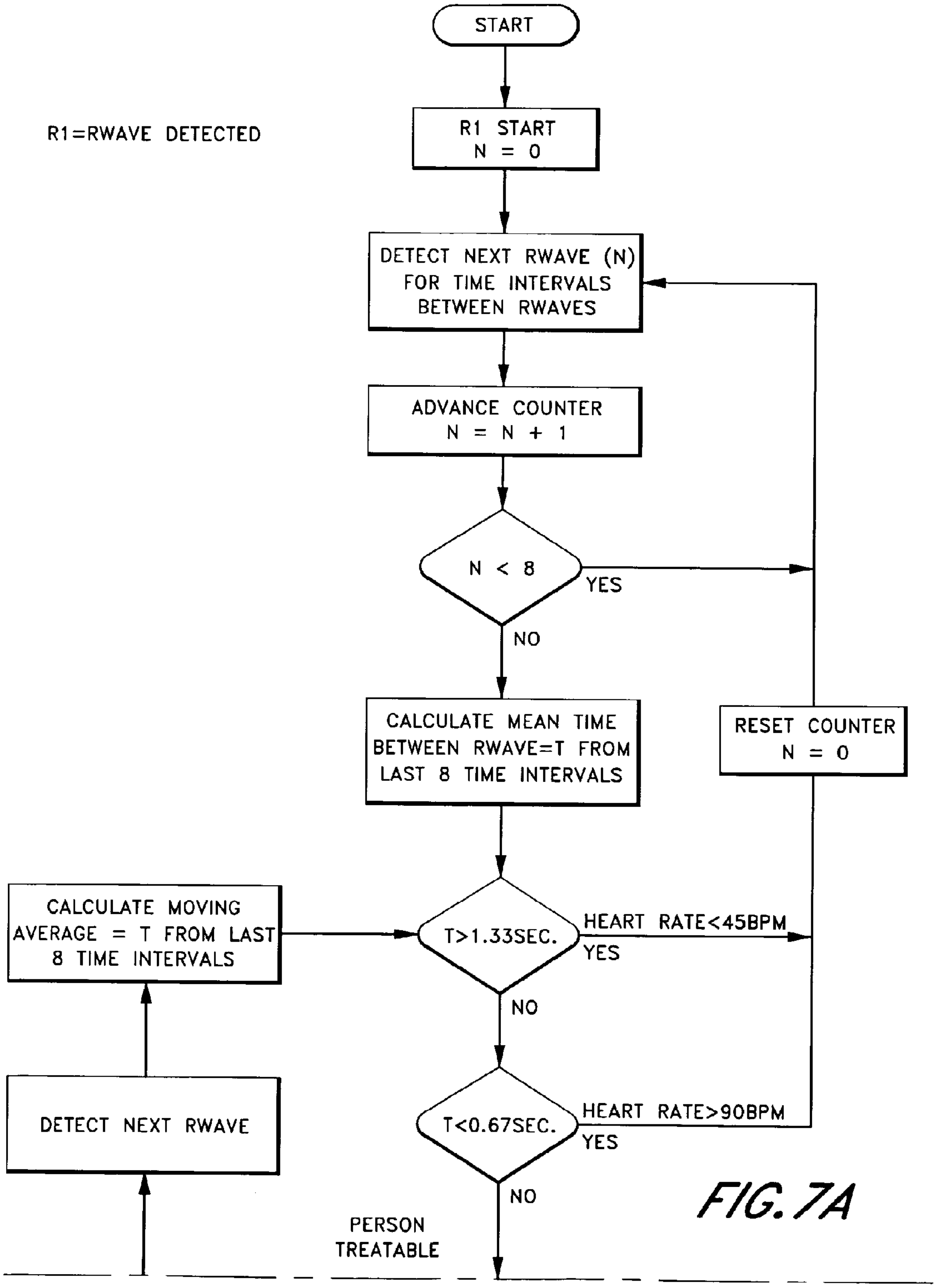
Figure 7B:
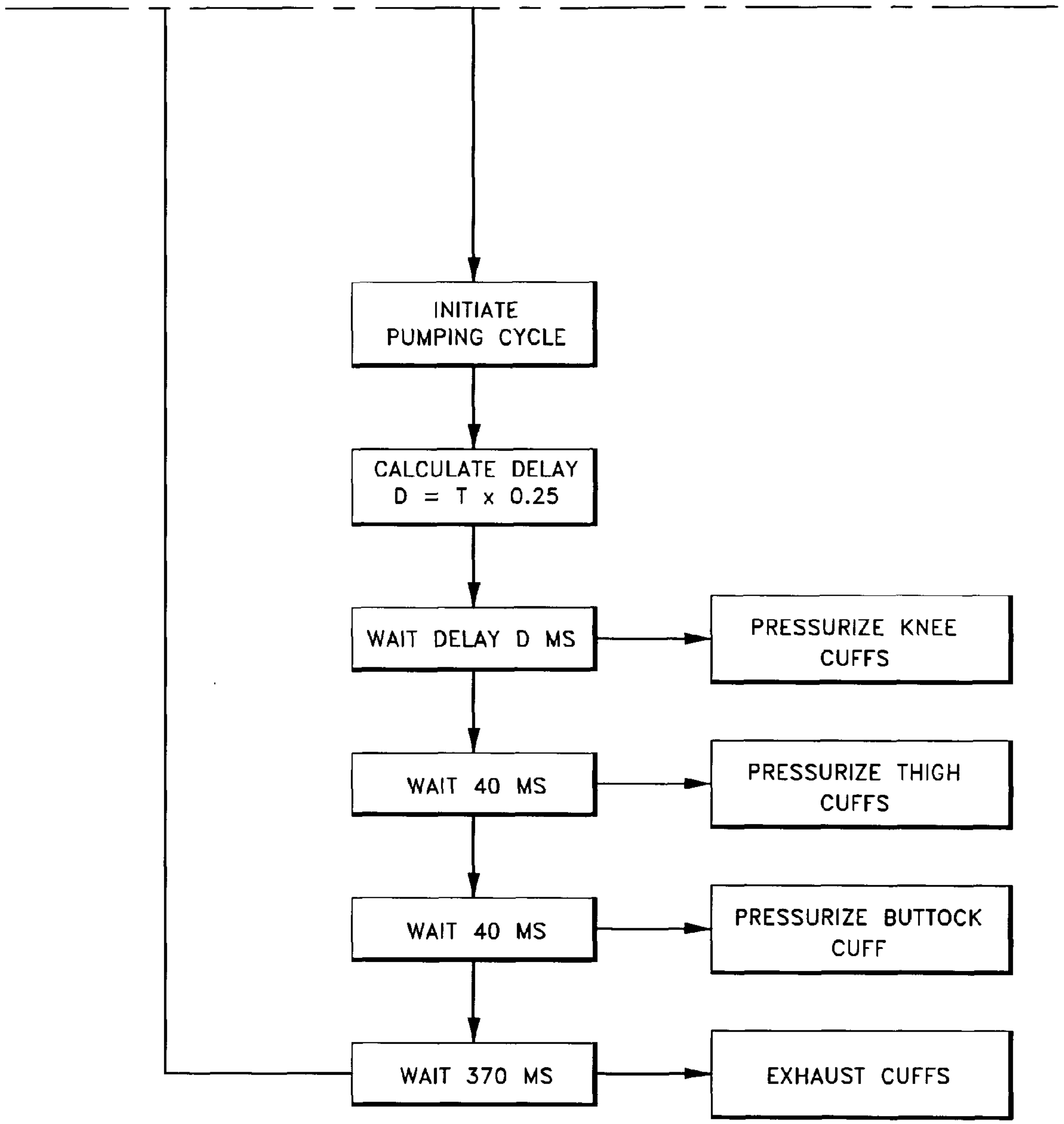

FIGS. 7A and 7B is a schematic representation of one embodiment of the programming of PLC 80. PLC 80 receives a squared ECG signal from ECG timing board 92. PLC 80 detects eight squared R wave signals and calculates the total time interval between the eight squared R wave signals. If the total time interval is greater than about 10.7 seconds or less than about 5.3 seconds, the R wave counter is reset and the total time interval is recollected. If the total time interval is between 5.3 and 10.7 seconds, PLC 80 initiates a pump cycle. Following a delay after the last detected peak in the squared ECG signal, PLC 80 initiates a first control signal that is transmitted to air valve 58 controlling bladders 64 at the lower thigh. In one variant of the invention, the delay is pre-set at about 280 milliseconds. Alternatively, the delay can be calculated based upon the patient's heart rate or peak-to-peak time interval based upon the EC signal. In another variant of the invention, the delay is about 25% of the average peak-to-peak interval of the last eight trailing QRS complexes. In still another variant, the delay is about 25% of the longest of the trailing eight peak-to-peak intervals of the ECG signal. After a fixed interval set at about forty milliseconds, a second control signal to air valve 58 controlling bladders in the upper thigh/inguinal regions is initiated. Optionally, first control signal to air valve 58 controlling bladders 64 of the lower thighs may be terminated after the second control signal is initiated. The early termination of the first control signal advantageously allows earlier filling of the thighs for the next pump cycle. There may be a slight delay between the initiation of the second control signal and the termination of the first control signal to allow bladders 64 of the upper thigh to fully inflate before deflating bladder 64 at the lower thigh. After another fixed interval of about 40 milliseconds, a third control signal to air valve 58 controlling the buttock bladders is initiated. After a fixed interval set at about 370 milliseconds after the start of the third control signal, the three control signals are terminated and the cycle is repeated. Preferably, the control signals continue for the pre-set interval irrespective of whether another ECG signal or PVC is detected during the transmission of the control signals. Alternatively, PLC 80 can terminate the signal cycle if another signal peak is detected and initiate the next cycle, but does not distinguish between squared sinus QRS complexes and squared PVC's. Although the preferred embodiments of the invention have described the use of ECG timing board 92 and PLC 80 to process ECG signals and provide control signals to the valves, one skilled in the art will understand that computers, microprocessors and other electronic controllers can also be used to process ECG signals and provide control signals. One skilled in the art will understand that variations of the above control systems, or other known ECP control algorithms, may be used to practice the invention.

Figure 8:
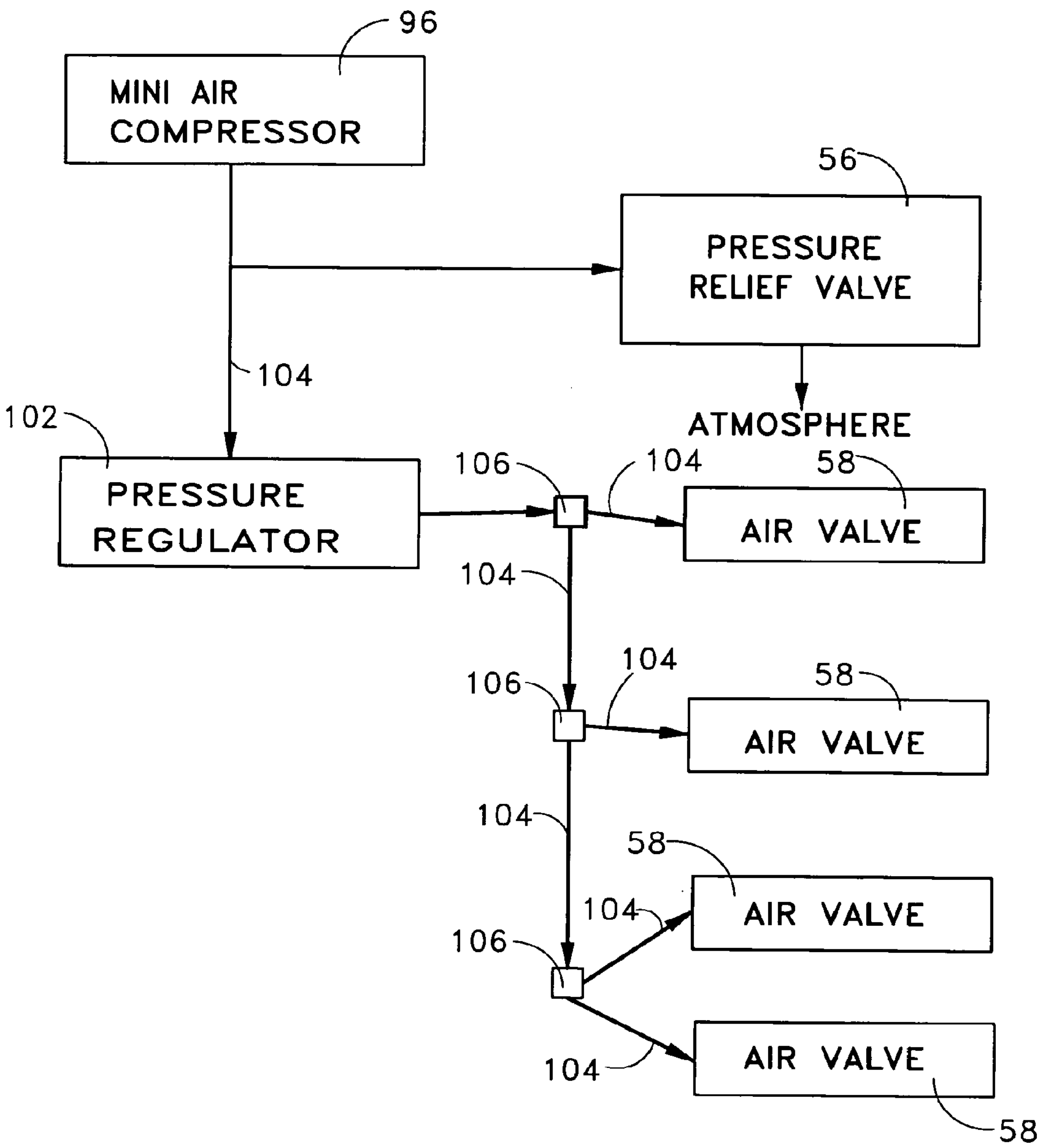
FIG. 8 shows a schematic of one embodiment of the invention comprising a mini air compressor that provides air pilot assist to the valves of the ECP system.

FIG. 8 represents one embodiment of a mini air system used for providing pilot assist air to the air valves 58. Mini air compressor 96 is a 24-volt mini compressor with an output of about ½ cfm at a pressure of about twelve psi. Mini air compressor 96 connects to mini air compressor pressure relief valve 100 which is set to vent air at about twelve psi. Mini air compressor pressure relief valve 100 connects to mini air compressor pressure regulator 102. Air pressure regulator 102 is a ¼ inch pipe fitting set at about ten psi. The output from mini air compressor pressure regulator 102 feeds the actuators of at least one air valve 58 using at least one ¼ inch air line tee 106 and ¼ inch air line 104. By providing a separate and smaller compressor to produce the higher-pressure smaller-volume pilot assist air for driving the pilot assist air valves, air compressor 50 is not unnecessarily producing higher pressure for bladders 64. Thus, air compressor 50 thus can operate efficiently at lower pressures independent of the higher pressure used for the pilot assist air needed by valves 58. By having two different compressors for serving two different functions, the total amount of noise, heat and patient discomfort created by the ECP system is reduced. In the embodiments of the invention that do not use pilot air assist valves, a mini air system is not required.

Figure 9A:
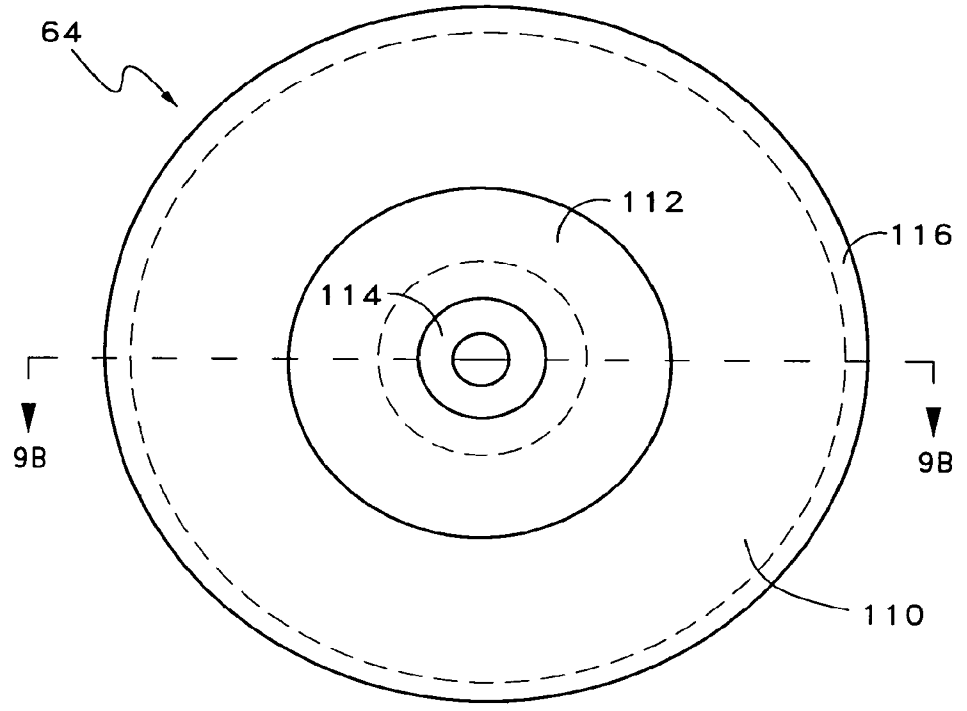
FIGS. 9A and 9B are superior and side views of one embodiment of the inflatable bladder.
Figure 9B:
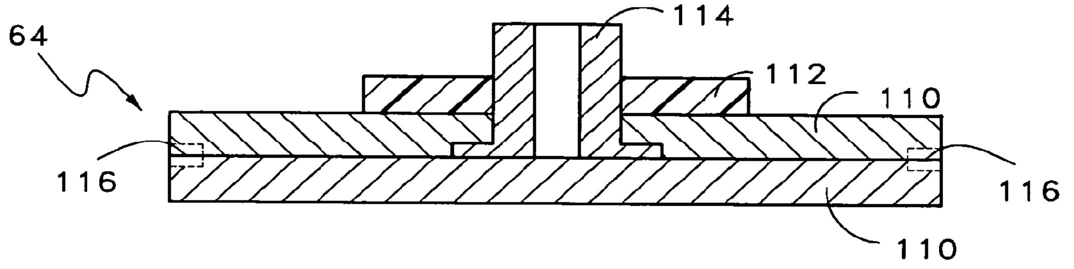

FIGS. 9A and 9B show one embodiment of bladder 64 used in ECP system 22. Bladder 64 comprises a bladder connector 114 attached to a first bladder wall 110. Bladder connector 114 has an internal diameter of about ¼ inch to about ¾ inch. First bladder wall 110 is sealed to a second bladder wall 110 along a bladder sealing area 116 along the edges of bladder walls 110. Bladder sealing area 116 is approximately about ⅛ to about ⅜ inch wide. Attaching is done in a manner to provide a hermetic seal and to withstand about a ten psi or more inflation pressure. Hermetic sealing may be performed by heat sealing, solvent sealing, adhesives, or any of a variety of hermetic sealing methods known in the art and incorporated by reference herein. In another embodiment, a single continuous bladder wall forms bladder 64. A hook fastener ring 112 attaches to the area surrounding bladder connector 114. Hook fastener ring 112, including but not limited to those made by Velcro USA (Manchester, N.H.), facilitates affixation of bladder 64 to cuffs described below. FIG. 9A depicts balloon 64 with a circular shape, but other possible balloon shapes include square, rectangular, triangular or any other closed loop shape. A triangular balloon shape may be particularly suited for compressing the body in areas with creasing. The surface area of bladder 64 when flat is about forty square inches on one side. In another embodiment, the surface area is from about twenty square inches to about sixty square inches. Bladders 64 may be made from polyester, polyurethane, polyvinylchloride, polyethylene or any of a variety of airtight materials known in the art and herein incorporated by reference.

Figure 10A:
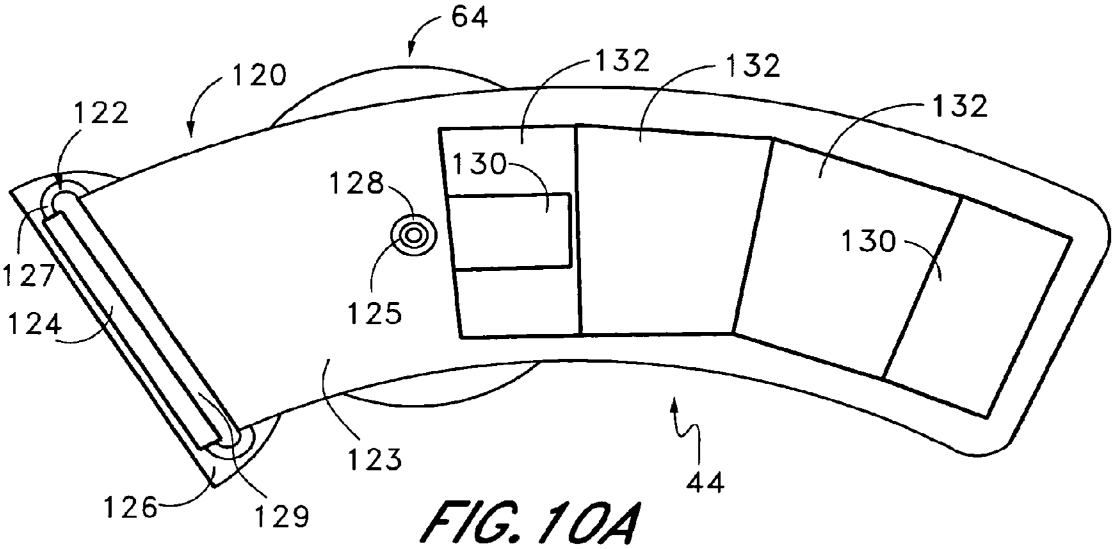
FIGS. 10A and 10B show the outer and inner surfaces of one embodiment of a leg cuff.
Figure 10B:
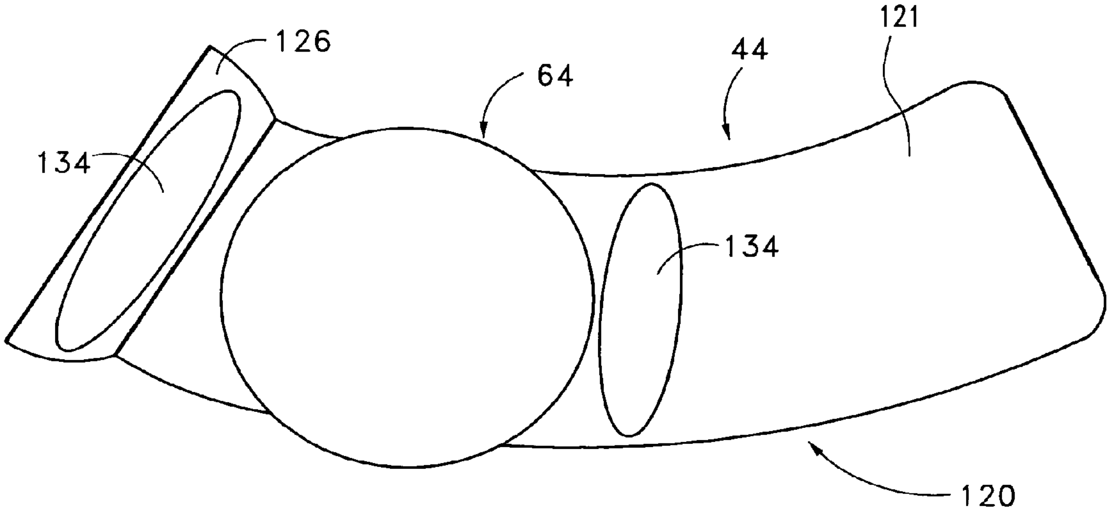

FIGS. 10A and 10B depict one embodiment of a left leg cuff 44 with bladder 64 in place. In this embodiment and in other embodiments described below, a right leg cuff 42 may be a mirror image of left leg cuff 44 for use on the right lower extremity. Alternatively, right leg cuff 42 and left leg cuff 44 may be identical or similar in configuration. Cuff material 120 has an inner surface 121, an outer surface 123 and a hole 125 for insertion of bladder connector 114 of bladder 64. Cuff 44 has an arcuate configuration that is particularly suited to compress anatomical structures that are located in areas of narrowing or creasing, but is not limited to this particular purpose. Cuff material 120 is advantageously made of a flexible non-stretch material that is able to withstand repeated inflations of bladder 64. In one embodiment, the non-stretch material comprises a 600 denier polyester cloth as used in backpacks. A ring 128 around hole 125 is optionally color-coded to indicate which complementary color-coded bladder air line 48 connects to that bladder 64. A portion of bladder 64 may be visible when viewing outer surface 123 of leg cuff 44, which may facilitate accurate placement of bladder 64 when securing cuff 44 to the patient. Outer surface 123 may also have identifying marks to show the position of underlying bladder 64 if obscured by cuff 44. Identifying marks will allow accurate positioning of bladder 64 on the patient's body.

A buckle 122 with a buckle roller 124 attaches to one end of cuff 44. Buckle 122 comprises a frame 127 with a slot opening 129 for insertion of a cuff end, the slot opening 129 having dimensions of about ¼ inch to about ¾ inch in one direction and about six inches in second direction. Buckle roller 124 is a tube with an internal diameter larger than the diameter of buckle frame 127, permitting buckle roller 124 to turn freely. Buckle roller 124 can reduce the effort needed to tighten cuff 44 on the patient by allowing cuff 44 to slide through the slot opening of buckle 122 with reduced friction against buckle frame 127. Buckle 122 and buckle roller 124 are made from any of a variety of rigid materials well known in the art, including but not limited to a metal or a plastic. Buckle shield 126 may be made of the same type of material as cuff material 120. Optionally, buckle shield 126 may be made stiffer with any of a variety of materials attached or adhered to buckle shield 126, including but not limited to a thin polycarbonate. Buckle shield 126 attaches to the inner surface 121 of cuff material 120 to provide protection from buckle 122. Buckle shield 126 may reduce the pinching of the skin on the patient when left leg cuff 44 is tightened. Hook fastener 130 and loop fastener 132 are attached to the other end of cuff material 120 by stitching, gluing, or any of a variety of methods well known in the art and incorporated by reference herein. Hook fastener 130 and loop fastener 132 are used to fasten right leg cuff 42 or left leg cuff 44 when the cuff is tightened on the patient. In one embodiment, the width of right leg cuff 42 or left leg cuff 44 is approximately six inches with a circumferential length of approximately 30 to 45 inches. In another embodiment, cuffs 42, 44 have a width of about three inches to about eight inches and a circumferential length of about twenty to about sixty inches. Cutouts are optionally provided in cuff material 120 for vascular access or any other procedure requiring access to body areas covered by cuff material 120.

FIG. 10B illustrates one embodiment of the invention comprising a friction or non-slip material 134 on inner surface 121 of right leg cuff 42 or left leg cuff 44. Non-slip material 134 may be joined to cuff material 120 by stitching, gluing, coating or any other method of attachment as is known in the art. Non-slip material 134 may also an inherent characteristic of cuff material 120. Non-slip material 134 may comprise any of a variety of flexible materials with a coefficient of friction sufficient to resist slippage of the cuff, including but not limited to neoprene, rubber or texturized versions of cuff material 120. Those skilled in the art will be familiar with other known non-slip materials that may be used.

Figure 10C:
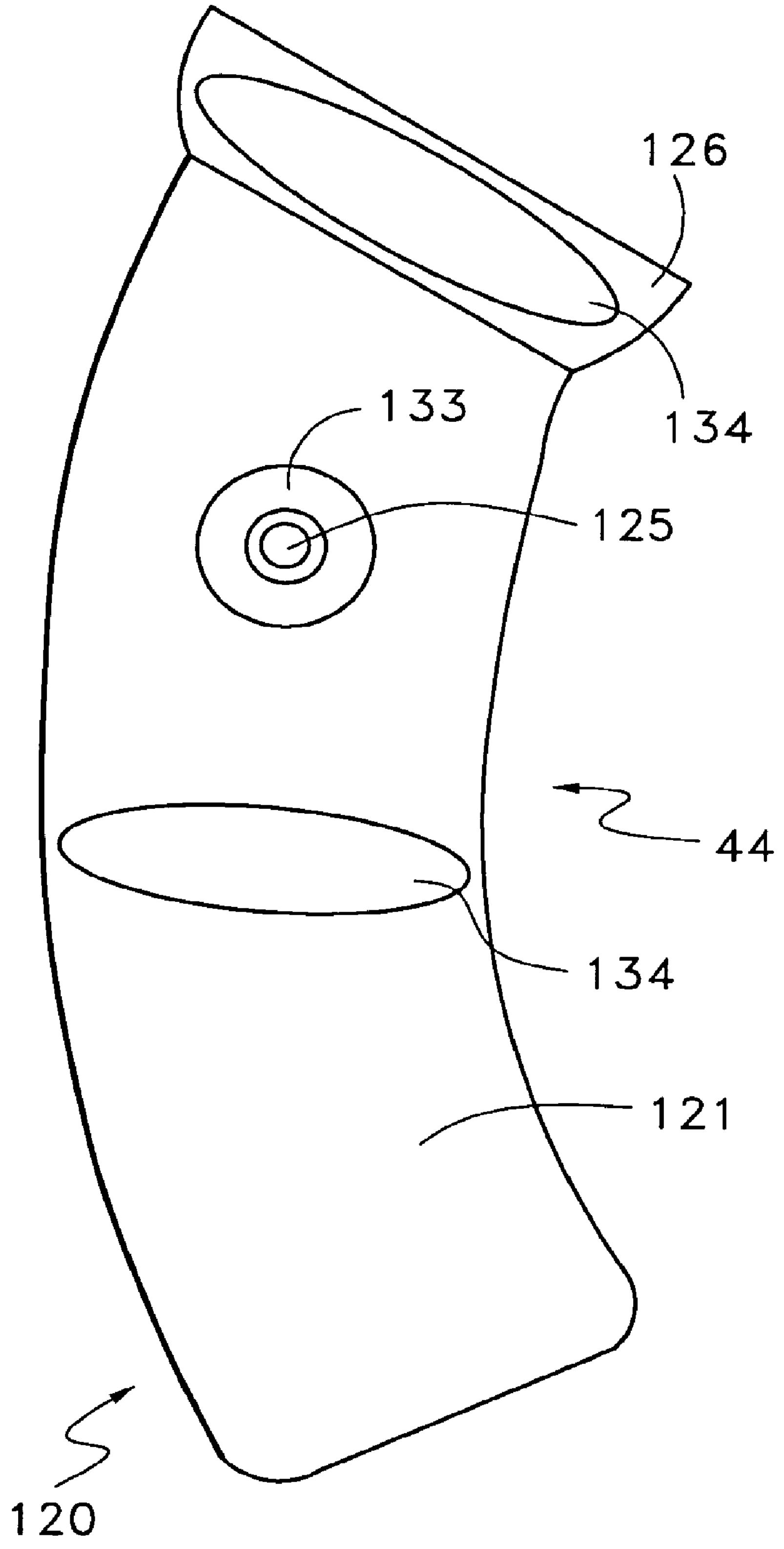
FIG. 10C shows the leg cuff of FIG. 10B without a bladder.

FIG. 10C shows inner surface 121 of cuff 44 without bladder 64. To attach bladder 64 to cuff 44, bladder connector 112 of bladder 64 inserts through hole 125 such that hook fastener ring 112 of bladder 64 engages loop fastener ring 133 on cuff 44.

Figure 11A:
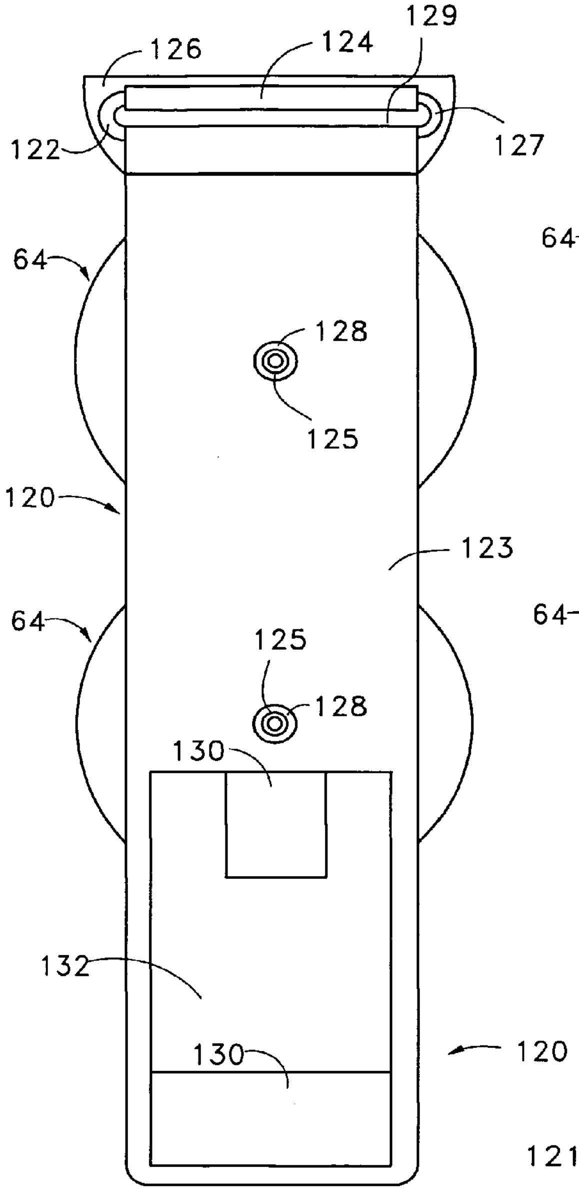
FIGS. 11A and 11B show the outer and inner surfaces of one embodiment of a buttock cuff.
Figure 11B:
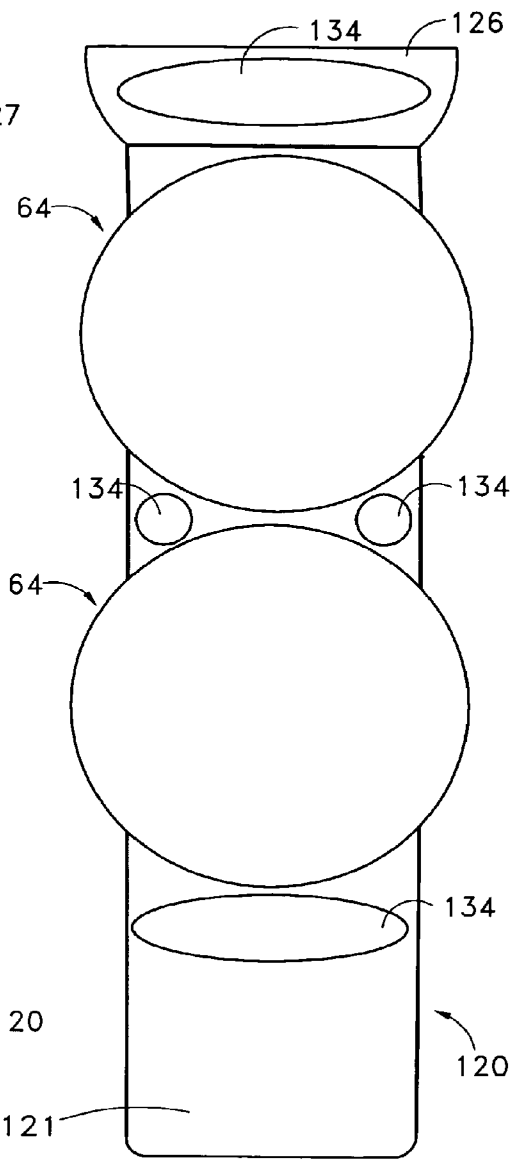

FIGS. 11A and 11B show one embodiment of the invention comprising a buttock cuff 46 with two bladders 64 attached to cuff 46. Cuff material 120 has an inner surface 121, an outer surface 123 and a hole 125 for insertion of bladder connector 114 of bladder 64. Buttock cuff 46 preferably has a straight configuration, but may also be arcuate or any other configuration that is able to encompass a circumference of the body that includes the buttocks. Cuff material 120 is made of any flexible non-stretch material able to withstand repeated inflations of bladder 64. In one embodiment, the non-stretch material comprises a 600 denier polyester cloth as used in backpacks. Rings 128 around holes 125 are optionally color-coded to indicate which complementary color-coded bladder air lines 48 are to be connected to bladders 64. A portion of bladders 64 may be visible when viewing outer surface 123 of buttock cuff 46, which may facilitate accurate placement of bladders 64 when securing cuff 46 to the patient. Outer surface 123 may also have identifying marks to show the position of underlying bladder 64 obscured by cuff 46.

In one embodiment, buttock cuff 46 comprises buckle 122 and optionally further comprises buckle roller 124 and buckle shield 126 as previously described. Cuff material 120 is made of any flexible non-stretch material able to withstand repeated inflations of bladders 64. In one embodiment, the non-stretch material comprises a 600 denier polyester cloth as used in backpacks. Hook fasteners 130 and loop fasteners 132 are attached to the other end of cuff material 120 by stitching, gluing, or any of number of methods well known in the art.

Hook fasteners 130 and loop fasteners 132 are used to secure buttock cuff 46 when cuff 46 is tightened on the patient. The width of buttock cuff 46 is approximately 6 inches with a circumferential length of about 60 inches. In another embodiment, cuff 46 has a width of about four inches to about ten inches and a circumferential length of about fifty to about ninety inches. In another embodiment, buttock cuff 46 comprises a plurality of bladders 64 from about one bladder 64 to about four bladders 64. Cutouts are optionally provided in cuff material 120 for vascular access or any other procedure requiring access to body areas covered by cuff material 120. FIG. 11B depicts one embodiment of the invention comprising a non-slip material 134 on inner surface 121 of buttock cuff 46, as described in the previous leg cuff embodiment.

Figure 11C:
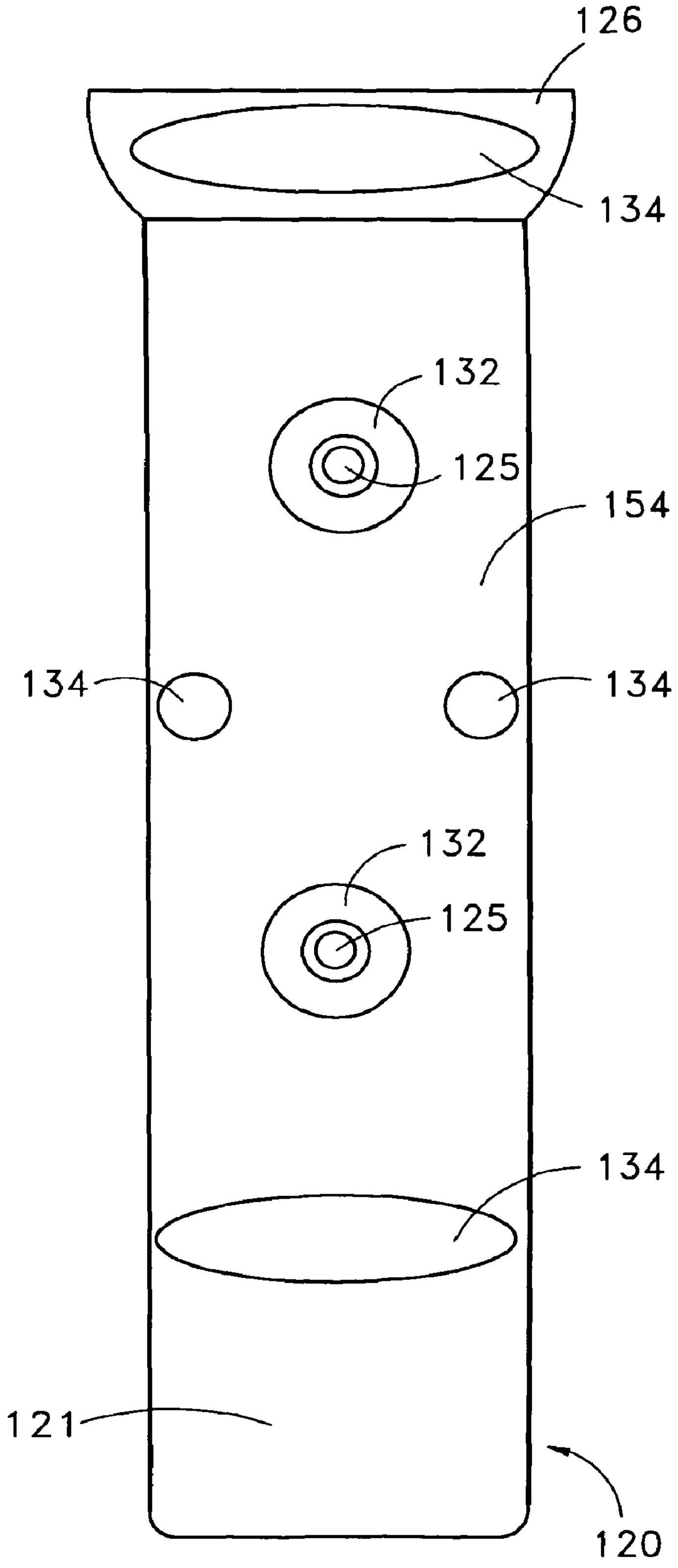
FIG. 11C shows the buttock cuff of FIG. 11B without a bladder.

FIG. 11C shows the inner surface of cuff 42 without bladders 64. Bladder connectors 112 of bladders 64 insert through holes 125 and rings 128 of cuff material 120 to attach to bladder air lines 48.

In an alternative embodiment of the invention, hook fastener 130 is attached to cuff material 120 at one end and one surface of cuffs 42, 44 and 46 and loop fastener 132 is joined to cuff material 120 at the opposite end and opposite surface, allowing securing of cuffs 42, 44, 46 to the patient by wrapping one end of a cuff over the other end of the same cuff to by coupling hook fastener 130 to loop fastener 132. Buckle 122, buckle roller 124 and buckle shield are not required in this embodiment of the invention.

Figure 12A:
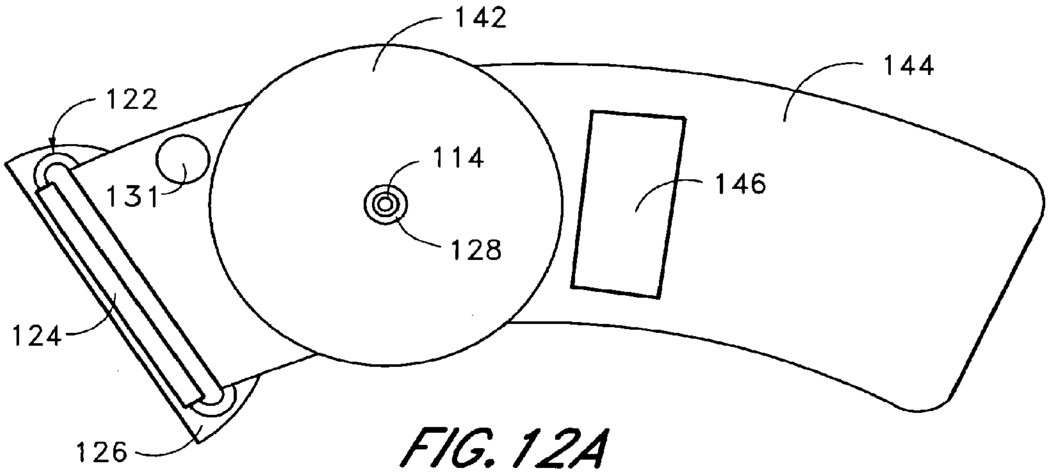
FIGS. 12A and 12B show the outer and inner surfaces of another embodiment of a leg cuff.
Figure 12B:
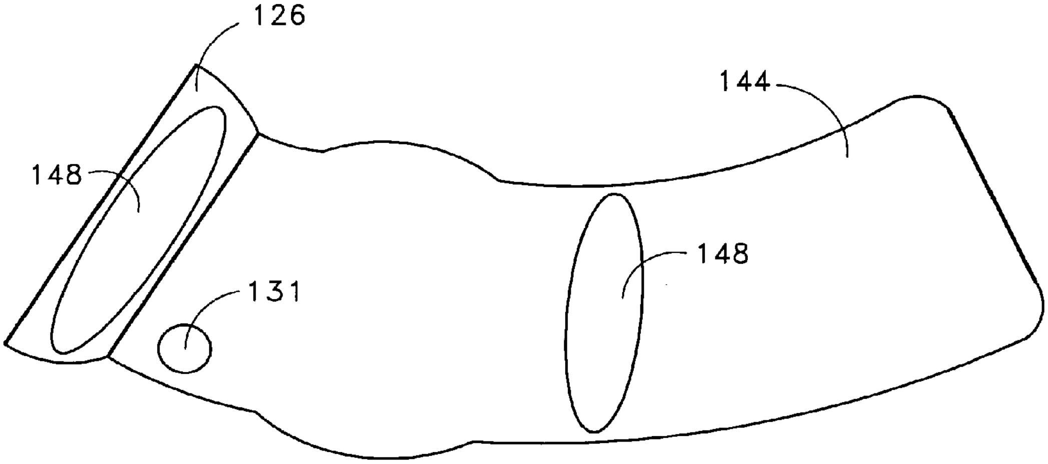

FIGS. 12A and 12B show another embodiment of a left leg cuff 150. Right leg cuff 156 may have a similar configuration or a mirror image configuration of left leg cuff 150, but is otherwise similar construction and materials. Optional color-coded ring 128 around bladder connector 114 indicates which color-coded bladder air line 48 is to be connected to which bladder connector 114. Bladder connector 114 is attached to bladder wall 142 by any of a variety of attachment methods including heat sealing, solvent sealing, gluing or any other hermetic sealing as known in the art. Bladder wall 142 is hermetically sealed to cuff material 144 using a sealing area of about ¼ inch on the outer edge of bladder wall 142, forming a bladder. In one embodiment, cuff material 144 is enlarged in width where bladder walls 142 are sealed to cuff material 144. Cuff material 144 may also have identifying marks to show the position of underlying bladder wall 142 obscured by cuff material 144. In another embodiment, the sealing area is about ⅛ to about ½ inch on the outer edge of bladder wall 142. Hermetic sealing may be performed by methods previously described. Bladder wall 142 and cuff material 144 comprise any of a variety of flexible non-stretch airtight materials, as previously described. Bladder wall 142 and cuff 144 may comprise different materials that are hermetically sealable together. Bladder wall 142 may comprise any of a variety of non-stretch or semi-stretchable airtight materials, including but not limited to polyurethane materials made by Magister Corporation (Chattanooga, Tenn.), herein incorporated by reference. Use of semi-stretchable airtight materials for bladder wall 142 may facilitate inward volume expansion and pressure transmission to the patient.

In one embodiment, leg cuff 150 comprises buckle 122 and optionally buckle roller 124 and buckle shield 126 as previously described. A self-adhesive hook 145 and loop fastener 146 is attached to cuff material 144 near bladder wall 142. In one embodiment, only one side of self adhesive hook and loop fastener 146 is attached to bladder wall 142. The topside of self-adhesive hook and loop fastener 146 is self-adhesive and covered with a wax paper-type protector. This allows the operator to remove the protector and adhere the end of left leg cuff 150 to the self-adhesive when securing the cuff to the patient. This configuration permits leg cuff 150 to be fitted to the patient and yet allows the removal of leg cuff 150 as medical needs dictate by separating the hook fastener from the loop fastener. In another embodiment, both hook fastener 130 and loop fastener 132 are preattached to leg cuff 150. The width of leg cuff 150 is approximately six inches with a length of approximately thirty to forty-five inches. In one embodiment, leg cuff 150 comprises self-adhesive non-slip material 148 on the inner surface of left leg cuff 150, of material and attached as previously described. Cutouts 131 are optionally provided in cuff material 144 for vascular access or any other procedure requiring access to body areas covered by cuff material 144. This embodiment may also be particularly suited for use as a disposable cuff because of the simplified design and lower cost of manufacturing, but the embodiment is not limited to this particular use.

Figure 13A:
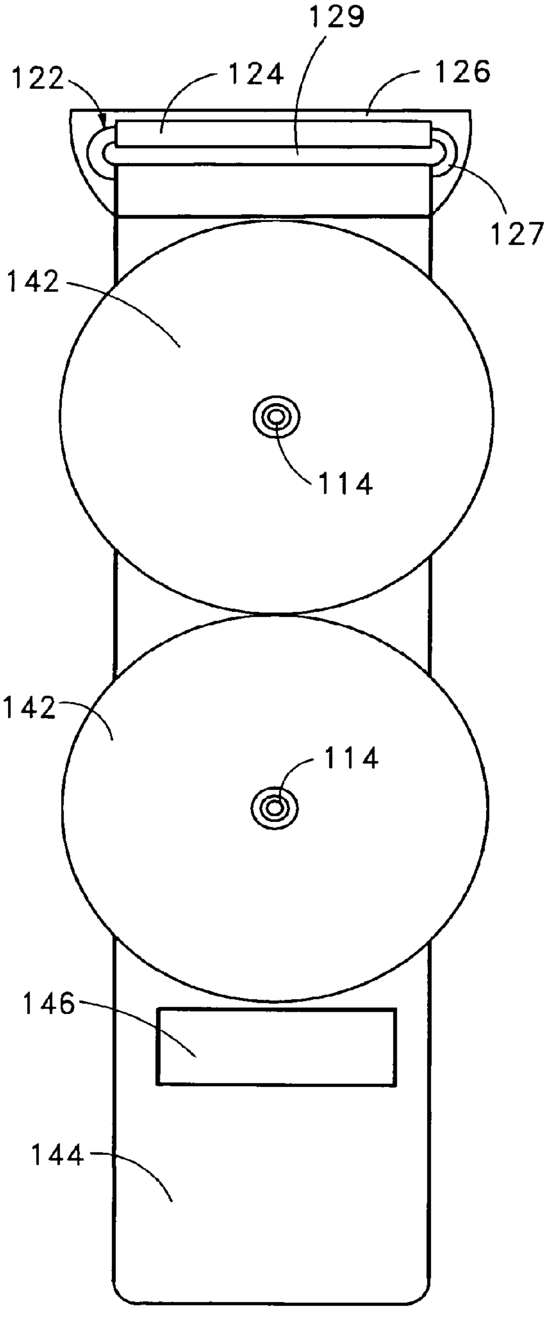
FIGS. 13A and 13B show the outer and inner surfaces of another embodiment of a buttock cuff.
Figure 13B:
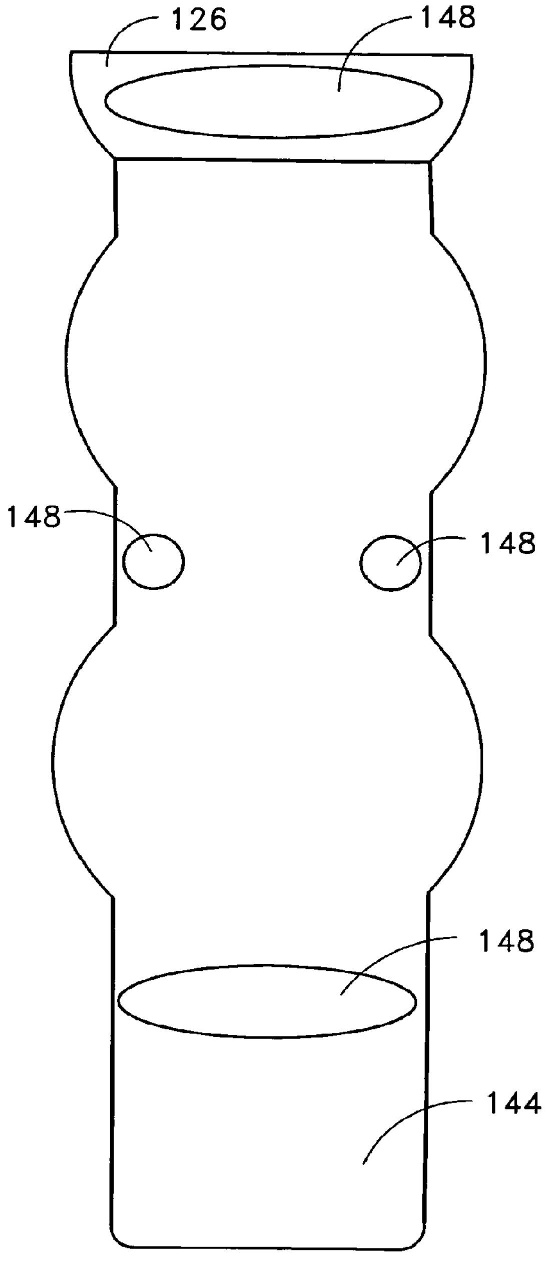

FIGS. 13A and 13B show another embodiment of the invention comprising a buttock cuff 154. Two bladder connectors 114 are provided in bladder walls 142. Optional color-coded rings 128 around bladder connectors 114 indicate which color-coded bladder air lines 48 are to be connected to which bladder connectors 114. Bladder connectors 114 are attached to bladder walls 142 by any of a variety of attachment methods including heat sealing, solvent sealing, gluing or any other hermetic sealing method as known in the art. Bladder walls 142 are hermetically sealed to cuff material 144 using a sealing area of about ¼ inch on the outer edge of bladder wall 142, forming a bladder. In another embodiment, the sealing area is about ⅛ to about ½ inch on the outer edge of bladder walls 142. In one embodiment, cuff material 144 is enlarged in width where bladder walls 142 are sealed to cuff material 144. Cuff material 144 may also have identifying marks to show the position of underlying bladder wall 142 obscured by cuff material 144. Hermetic sealing may be performed by heat sealing, solvent sealing, adhesives or any of a variety of hermetic sealing methods known in the art. Bladder walls 142 may comprise any of a variety of non-stretchable or semi-stretchable airtight materials known in the art. Use of semi-stretchable airtight materials for bladder wall 142 may facilitate inward volume expansion and pressure transmission to the patient.

In one embodiment, buttock cuff 154 comprises buckle 122 and optionally buckle roller 124 and buckle shield 126 as previously described. A self-adhesive hook 145 and loop fastener 146 is attached to cuff material 144. The outer surface of self-adhesive hook and loop fastener 146 is self-adhesive and covered with a wax paper-type protector. This allows the operator to remove the protector and adhere the end of buttock cuff 154 to the self-adhesive after tightening on the patient. This configuration permits buttock cuff 154 to be fitted to the patient and yet allows the removal of buttock cuff 154 as desired by separating the hook fastener from the loop fastener. In another embodiment, both hook fastener 145 and loop fastener 146 are pre-attached to buttock cuff 154. The width of buttock cuff 154 is about six inches with a length of about sixty inches. In one embodiment, buttock cuff 154 comprises self-adhesive non-slip material 148 on the inner surface of buttock cuff 154, of material and attached as previously described. Cutouts are optionally provided in cuff material 144 for vascular access or any other procedure requiring access to body areas covered by cuff material 144. This embodiment may also be particularly suited for use as a disposable cuff due to the simplified design and lower cost of manufacturing, but the embodiment is not limited to this particular use.

In an alternative embodiment of the invention, hook fastener is joined to cuff material 144 at one end and one surface of cuffs 150, 154, 156 and a loop fastener is joined to cuff material 144 at the opposite end and opposite surface. This configuration allows the securing of cuffs 150, 154, 156 to the patient by wrapping one end of a cuff over the other end of the same cuff. This embodiment does not require buckle 120 and may further simplify the cuff design and lower the cost of manufacturing.

Figure 14A:
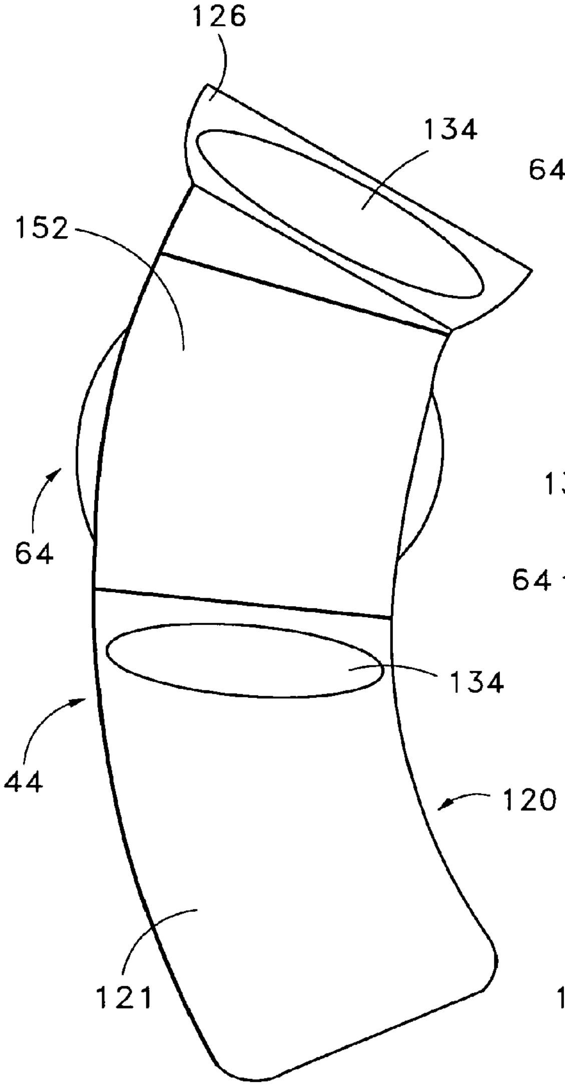
FIGS. 14A and 14B show the inner surfaces of still another embodiment of a leg and a buttock cuff with padding attached to the inner surface.
Figure 14B:
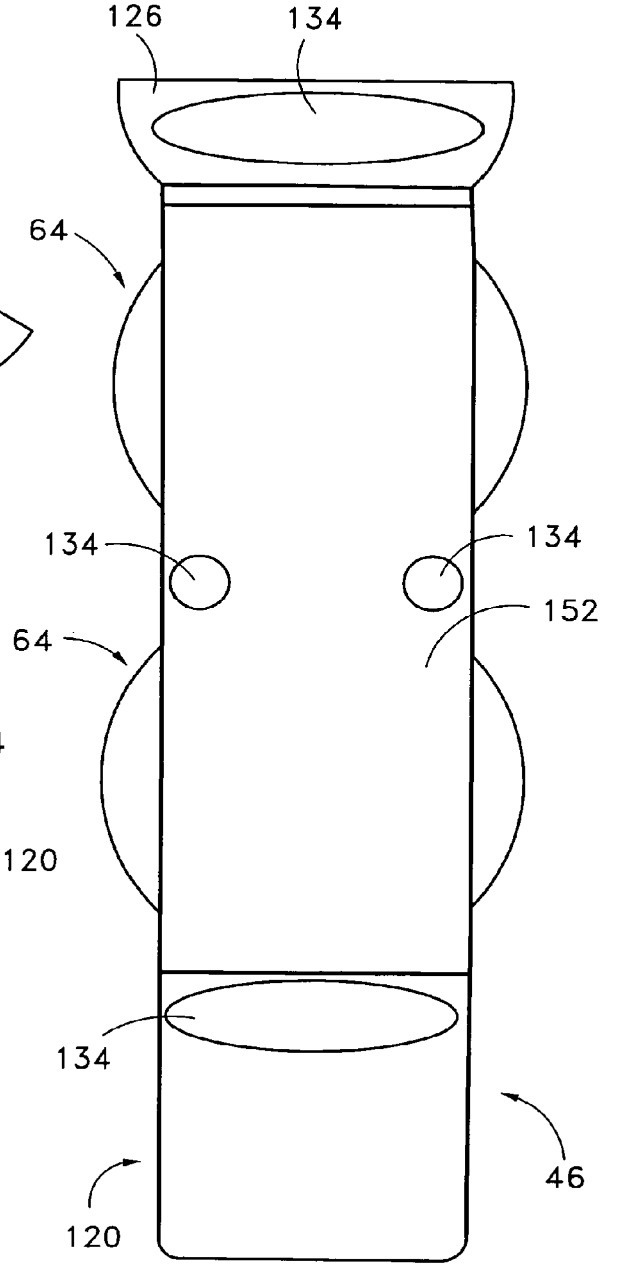

FIG. 14A shows one embodiment of the invention with a padding 152 placed on inner surface 121 of leg cuff 44. Padding 152 is a cloth, foam or encapsulated gel material used to reduce skin irritation resulting from multiple hours of treatment or in patients with sensitive skin. One skilled in the art will understand that any type of skin-protective covering or padding may be used. FIG. 14B shows the placement of padding 152 on buttock cuff 46.

Figure 15A:
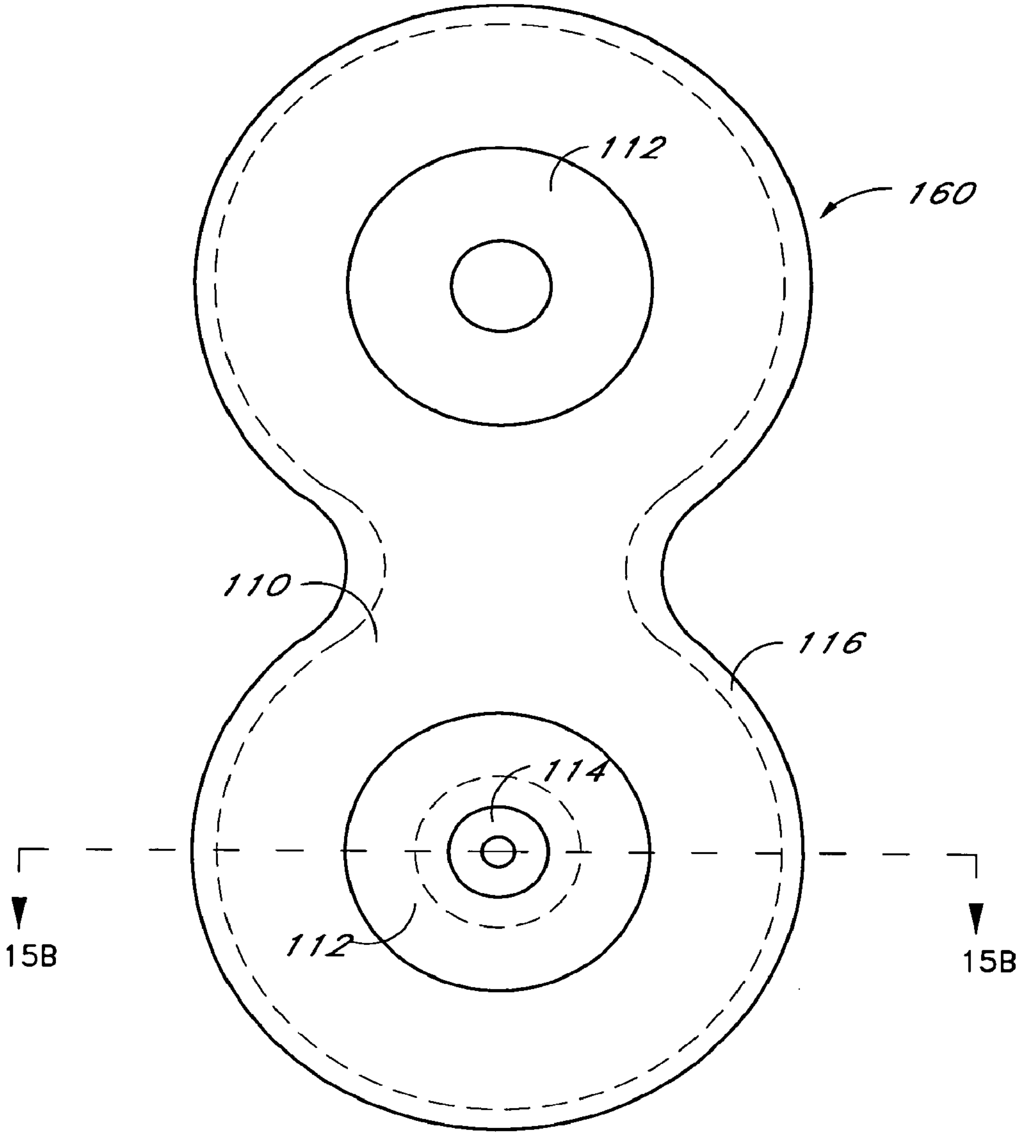
FIGS. 15A and 15B show an alternative embodiment of an inflatable bladder usable in a buttock cuff.
Figure 15B:
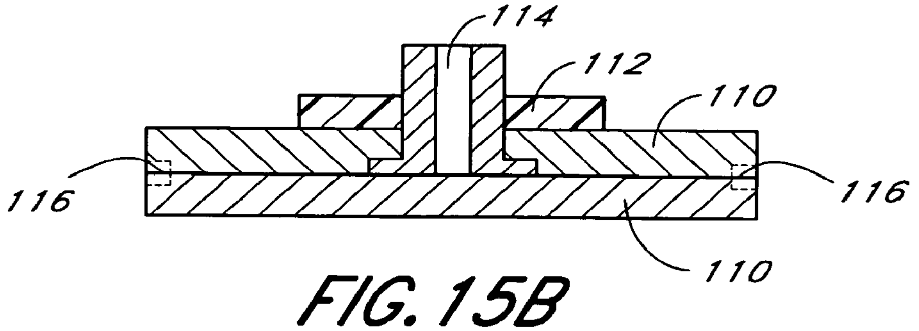

FIGS. 15A and 15B show another embodiment of a bladder comprising a single buttock bladder 158. One bladder connector 114 is attached to bladder wall 110 having an hourglass shape and a surface area of about seventy-two square inches. Although FIG. 15A depicts buttock bladder 158 with an hourglass shape, any closed loop shape may be used, including squares, rectangles, triangles or a combination thereof. A second bladder connector 114 may be optionally attached to the other portion of buttock bladder 158. Bladder connector 114 has an internal diameter of about ¼ inch to about ¾ inch. Bladder wall 110 is then hermetically attached to a second bladder wall 110 having an hourglass shape and a surface area of about seventy-two square inches. Attaching is done to provide an air tight seal and to withstand about ten psi inflation pressure. Bladder sealing area 116 is approximately about ⅛ inch to about ⅜ inch wide. Hook fastener ring 112 is adhered to the area surrounding bladder connectors 114. The surface area of single buttock bladder 158 when flat is about seventy-two square inches.

Figure 16A:
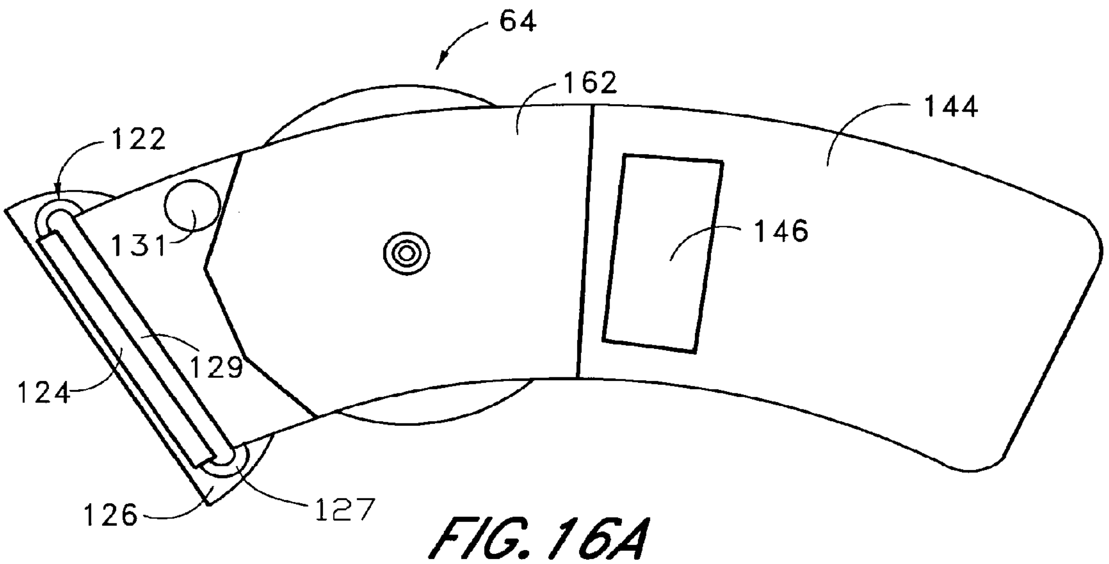
FIGS. 16A and 16B show the outer and inner surfaces of another embodiment of a leg cuff with a pocket for an inflatable bladder.
Figure 16B:
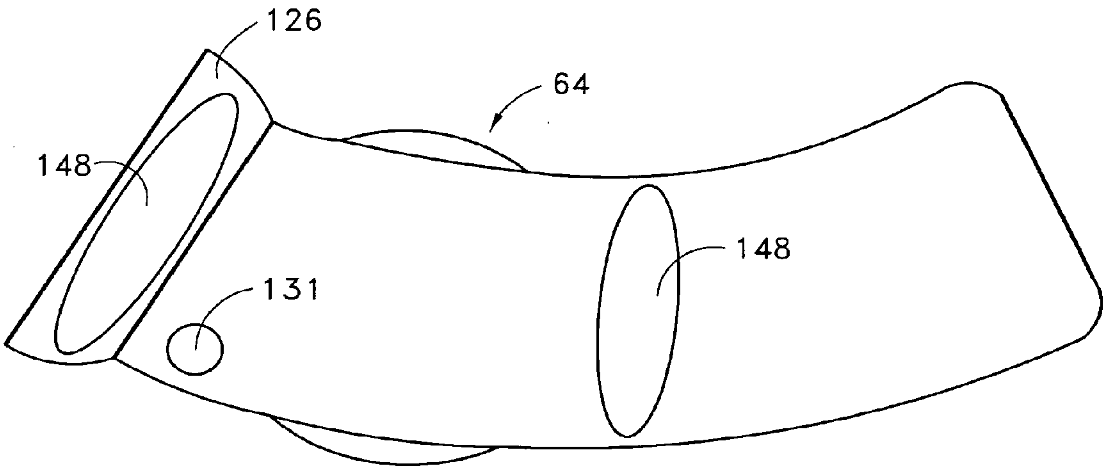

FIGS. 16A and 16B illustrate another embodiment of the invention comprising left leg cuff 150 with a leg bladder pocket 162 for holding and reversibly attaching bladder 64. Right leg cuff 156 is identical or similar to left leg cuff 150. Leg bladder pocket 164 comprises a flexible material attached to cuff material 144. In one embodiment, pocket 164 comprises the same material as cuff material 144. Cutouts 131 are optionally provided in cuff material 144 for vascular access or any other procedure requiring access to body areas covered by cuff material 144.

Figure 17A:
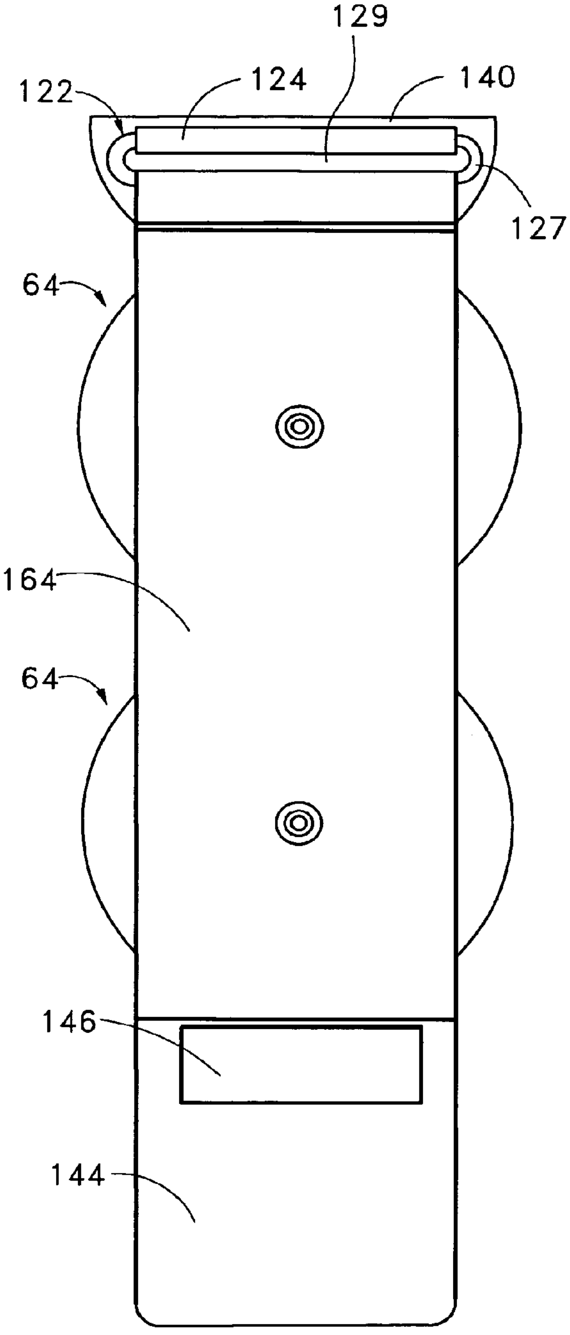
FIGS. 17A and 17B show the outer and inner surfaces of another embodiment of a buttock cuff with a pocket for an inflatable bladder.
Figure 17B:
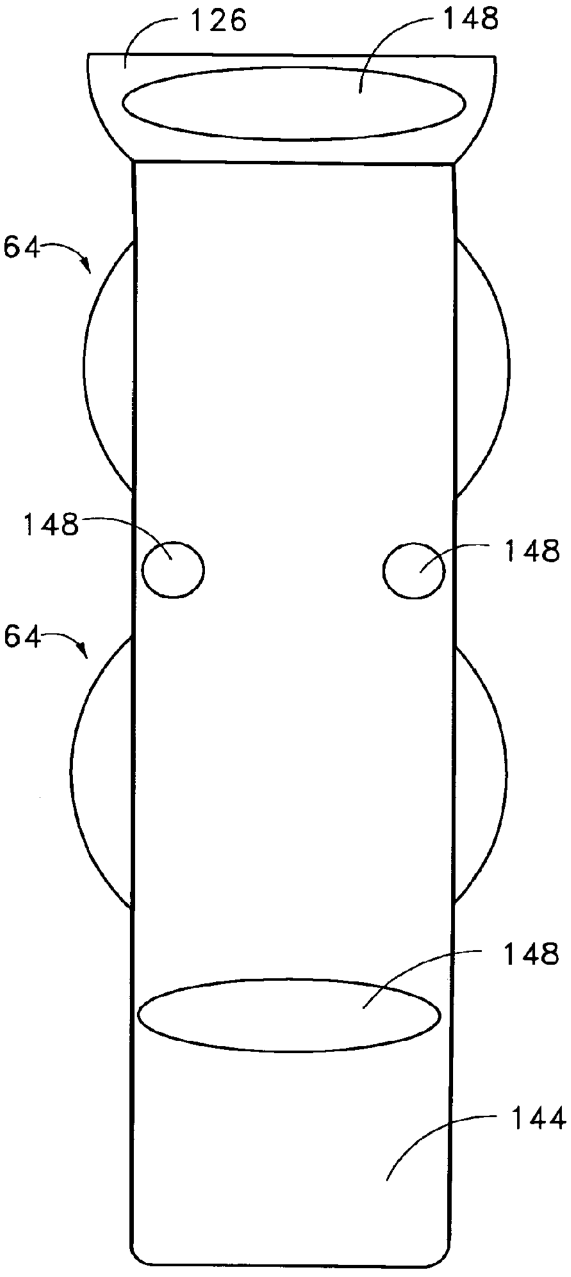

FIGS. 17A and 17B show another embodiment of buttock cuff 154 with an optional buttock bladder pocket 164 to allow the use of two bladders 64 or single buttock bladder 158. Buttock bladder pocket 164 is made of a flexible material able to be attached to cuff material 144. In one embodiment, pocket 164 comprises the same material as cuff material 144.

Although the preferred embodiments of the invention described above have used inflatable bladders and cuffs to provide the compression for ECP, one skilled in the art can adapt other compression mechanisms to provide ECP treatment using limited compression to the upper-posterior knees, inguinal regions and buttocks of a patient. For example, U.S. Pat. No. 6,620,116 to Lewis, herein incorporated by reference, discloses the use of electromechanical actuators in cuffs for compression. These electromechanical actuators can be adapted as ECP compression members to supply a total compression surface area of about 240 square inches or less to the upper-posterior knees, inguinal regions and buttocks.

Other embodiments of the invention include but are not limited to the use of other gases or liquids as an inflation fluid, including but not limited to water, nitrogen or helium. Helium has a lower fluid density and viscosity compared to atmospheric air and can advantageously provide higher fluid flow rates at the same pressures. Other gases or combination of gases may also be used. Because of the cost of helium, an embodiment of the invention using helium may further comprise a closed fluid system whereby deflation of the bladders occurs by venting the valves into a reservoir rather than to the atmosphere. One such closed system for ECP is disclosed in U.S. Pat. No. 6,572,621 to Zheng et al., herein incorporated by reference. The fluid vented to the reservoir is then recompressed and stored in air tank 52 for reuse in inflating bladders 64. Other alternative embodiments of the ECP system are described below.

In some embodiments of the invention, a temperature-controlled ECP system is provided. A temperature-controlled system may be desirable for some patients with skin conditions or for use in critical care or surgical environments, including but not limited to stroke treatment, hypothermia, cardiovascular surgery and neurosurgery. In one embodiment, heating and/or cooling coils may be embedded or applied to the cuffs or bladders. In a further embodiment of the invention, a reversible heat pump is attached to a set of temperature coils in the cuffs so that cooling or heating may be performed with the same set of coils. In another embodiment, the gas or liquid inflating the bladders may be cooled or heated to provide temperature control. Any of a variety of temperature control systems, as is known in the art, may be used to provide a temperature-controlled ECP system.

Figure 18:
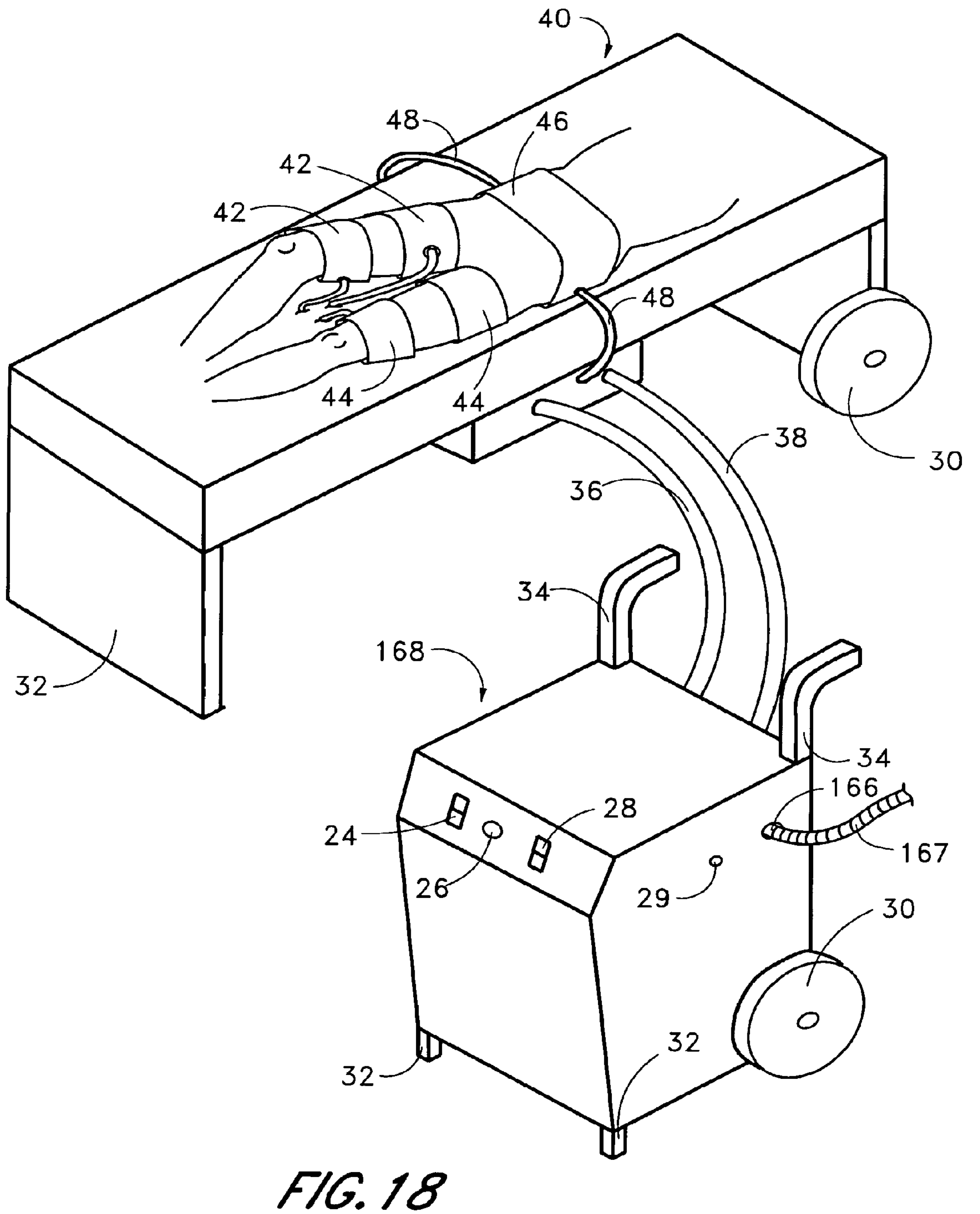
FIG. 18 depicts a patient connected to another embodiment of the ECP system with an inlet for connecting an external pressurized air supply.
Figure 19:
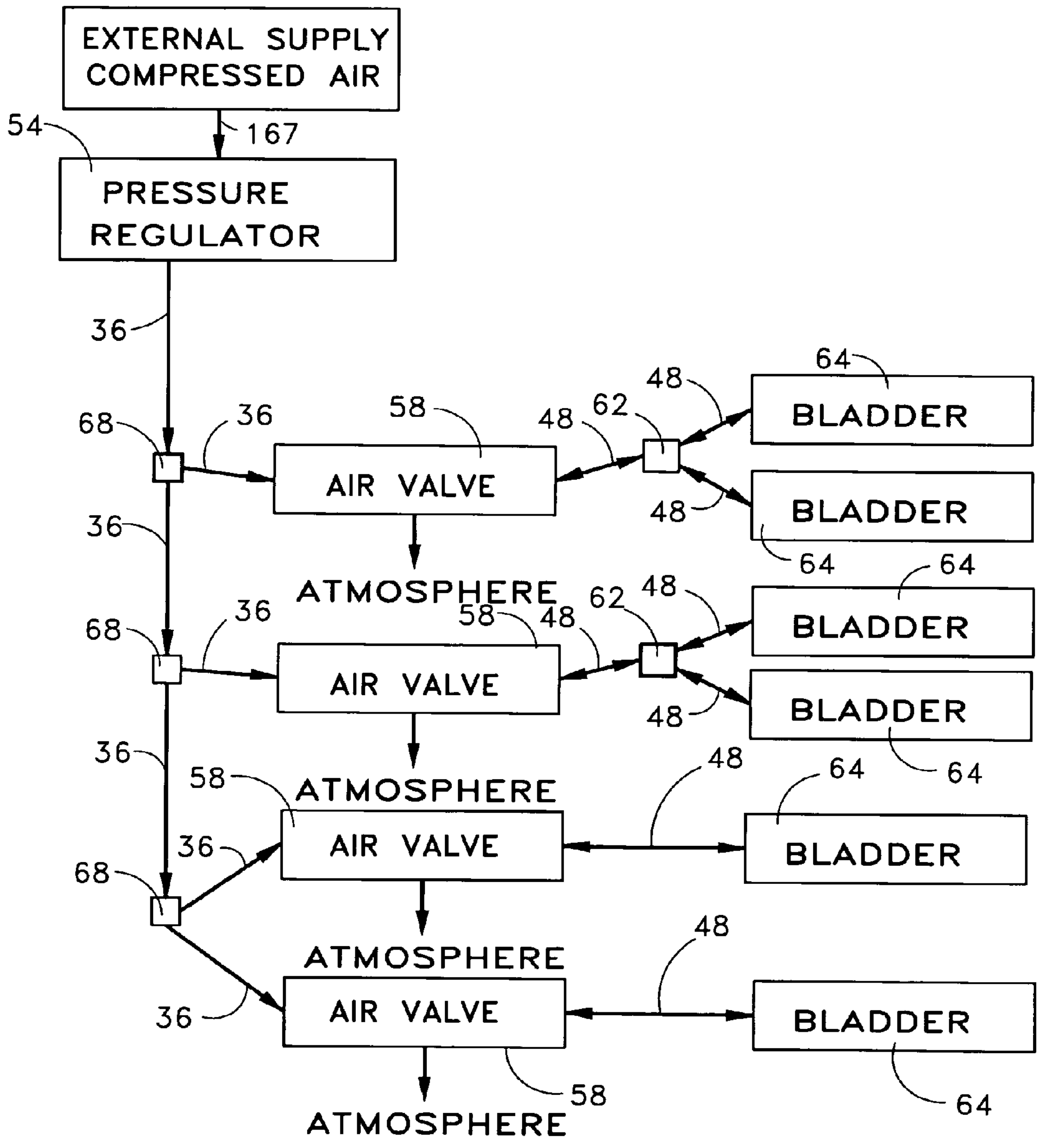
FIG. 19 depicts a schematic of the pressurized fluid system for the embodiment of the invention in FIG. 18.
Figure 20:
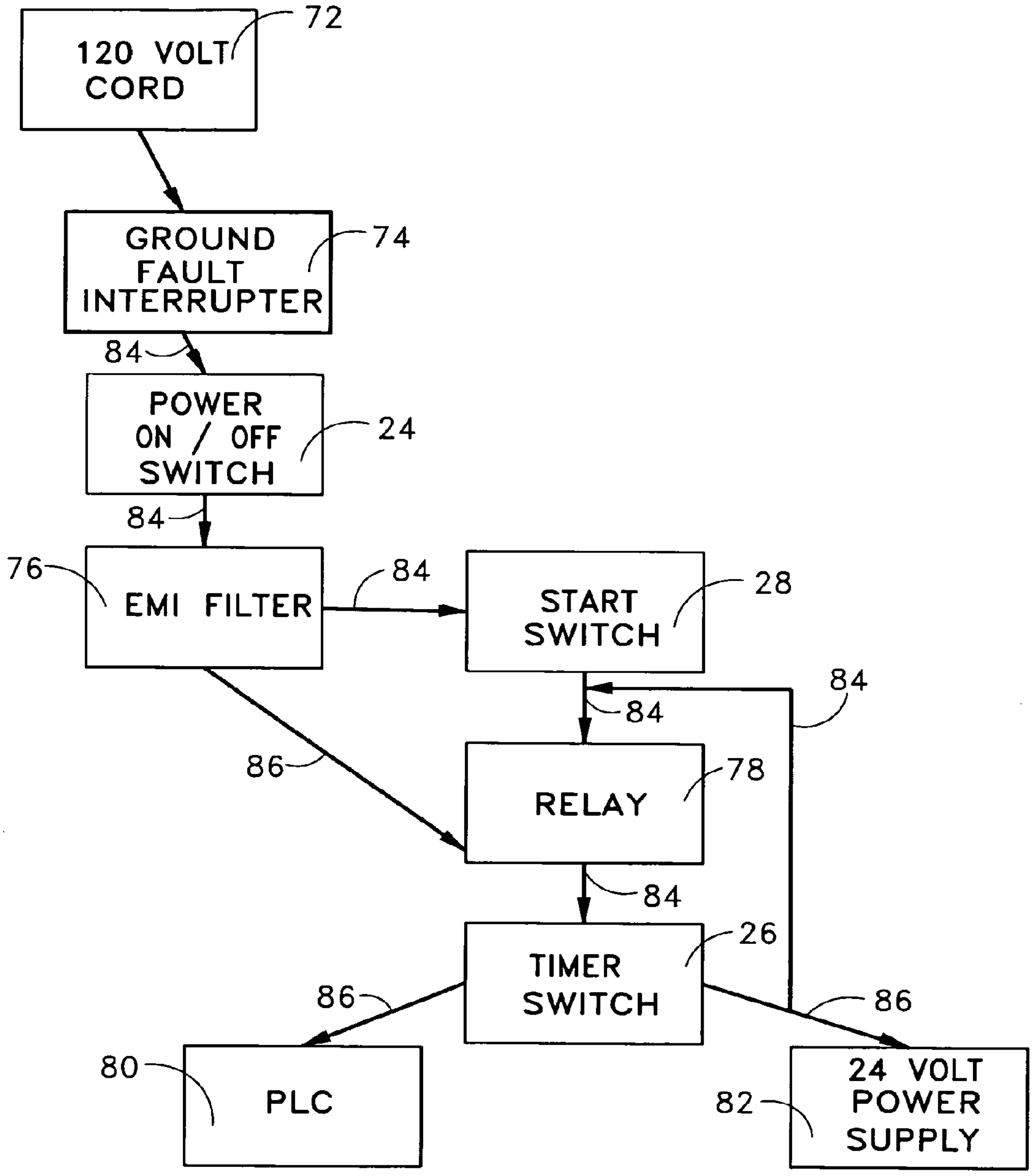
FIG. 20 illustrates a schematic of the 120-volt electrical system for the embodiment of the invention in FIG. 18.
Figure 21:
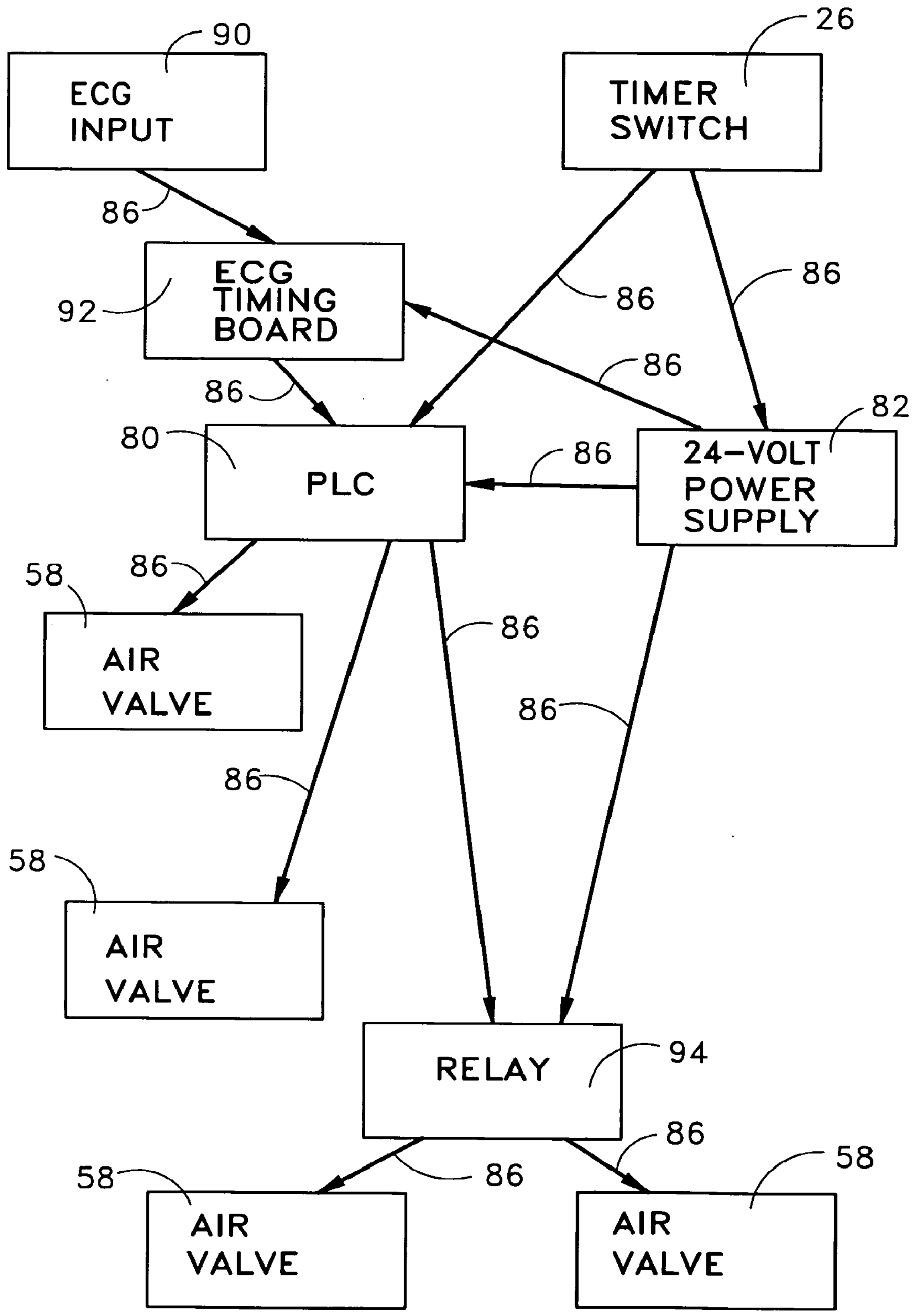
FIG. 21 is a schematic of the 24-volt electrical system for an embodiment of the invention shown in FIG. 18.
Figure 22:
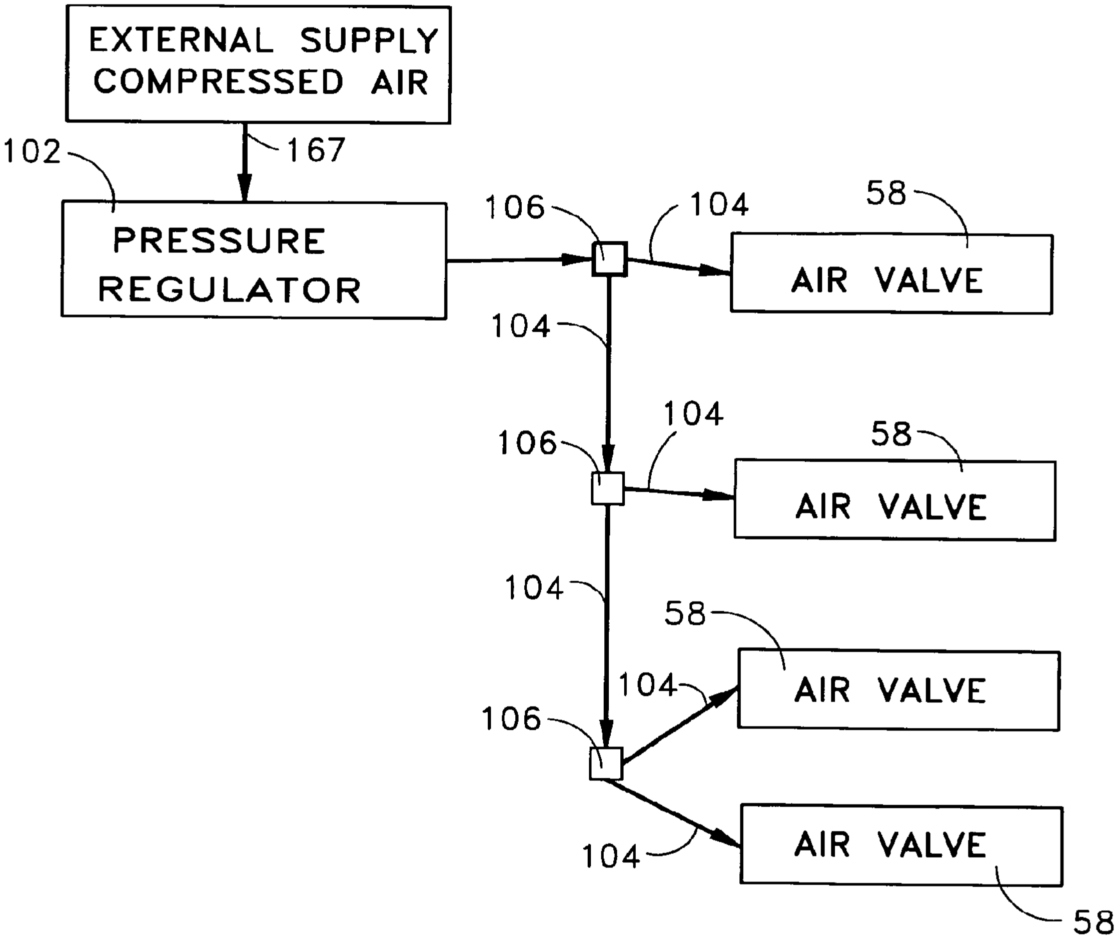
FIG. 22 shows a schematic of one embodiment of the invention in FIG. 18 wherein an external compressed air supply provides air pilot assist to the valves of the ECP system.

FIG. 18 represents another embodiment of the invention of ECP system 22 that is capable of using an external supply of compressed air. The external air supply tubing 167 is connected to external compressed air supply inlet 166 that is attached to pressure regulator 54. In one embodiment, ECP system 22 comprises air supply inlet 166 without air compressor 50. In another embodiment, ECP system 22 comprises both air supply inlet 166 and air compressor 50 and either source may be used to supply compressed air to bladders 64. FIG. 19 depicts a schematic of another embodiment of the invention using an external supply of compressed air. The air supply connects to air supply tubing 167 that attaches to pressure regulator 54. The remaining connections of this embodiment are otherwise similar to that shown in FIG. 3. FIG. 20 shows a schematic of the 120-volt electrical power system for this embodiment where external source of compressed air is utilized. Similarly, FIG. 21 shows a schematic of the 24-volt electrical system, without the mini air compressor. FIG. 22 is a schematic depicting the use of externally supplied compressed air for providing pilot assist air for air valves 58.

Figure 23:
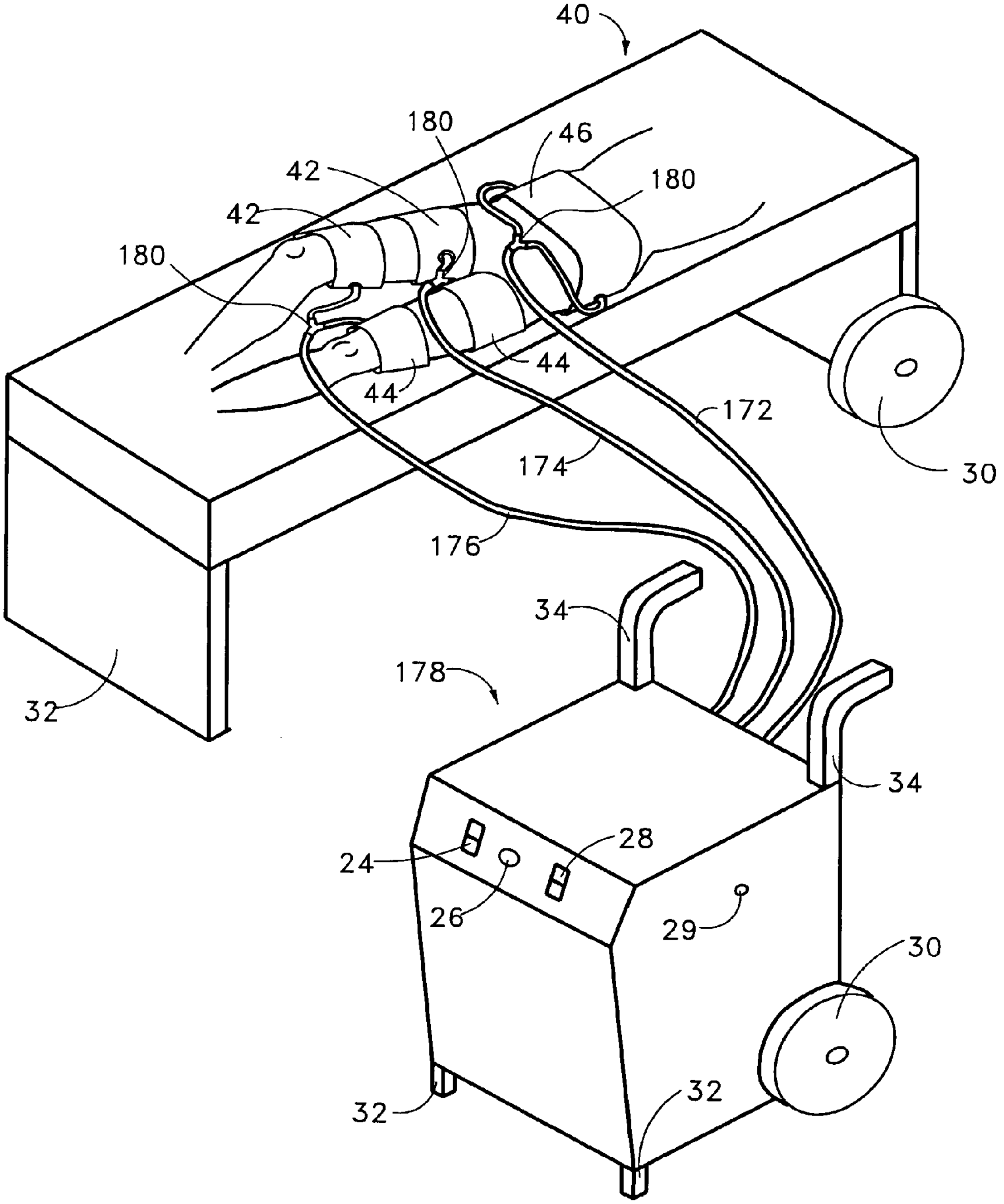
FIG. 23 depicts another embodiment of the invention wherein the air valves are integrated into the system so that a table is not required.
Figure 24:
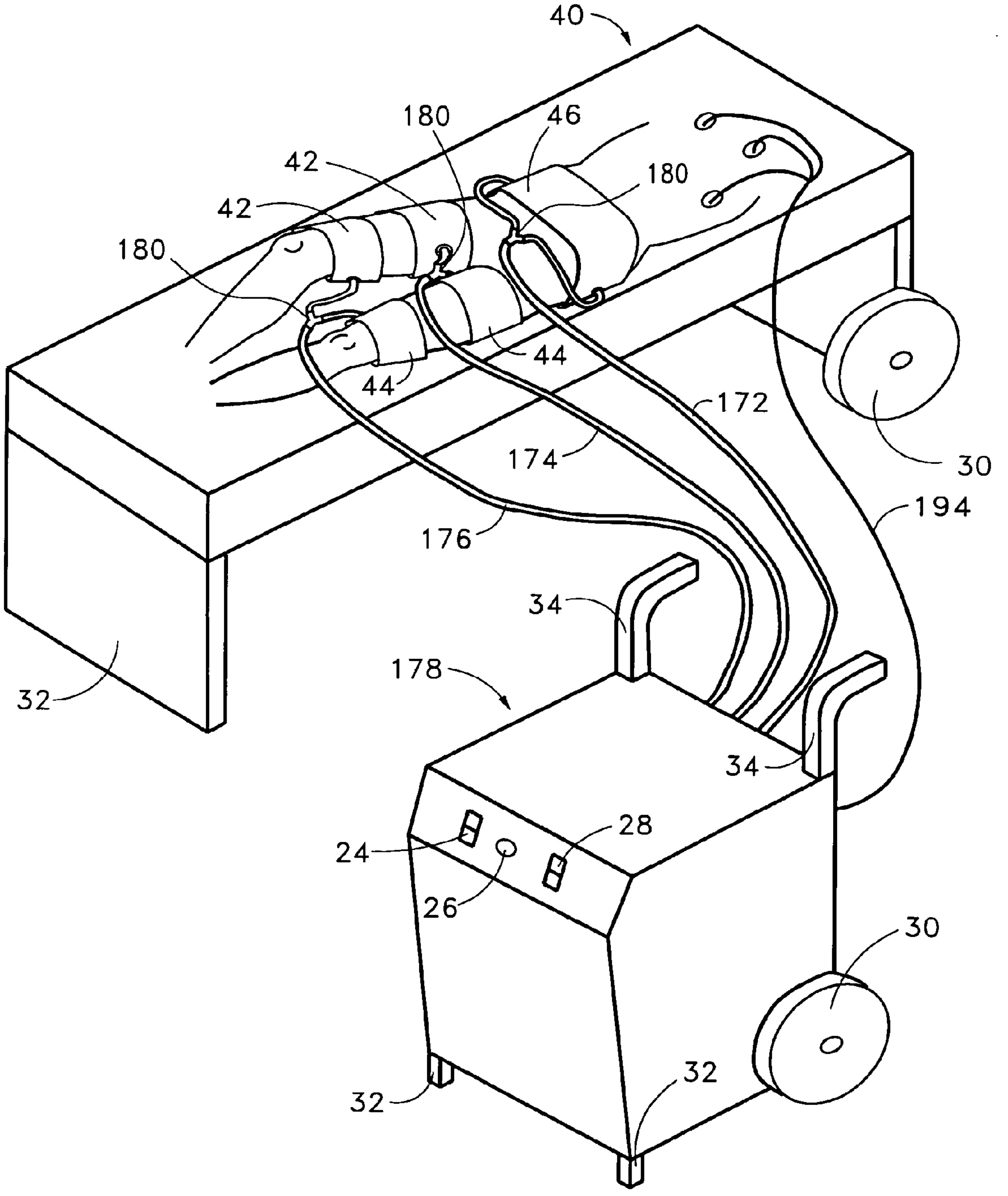
FIG. 24 depicts another embodiment of the invention with an integrated ECG monitor wherein the air valves are integrated into the system so that a table is not required.

FIG. 23 shows another embodiment of the invention where the air line, the control line and the valves are integrated into the housing of ECP system 178. Air hoses 172, 174 and 176 directly connect ECP system 178 to cuffs 42, 44 and 46, so that any surface, such as an hospital bed, may be used for patient treatment instead of table 40. Thus, patients do not have to be moved to a particular table to undergo treatment. Each hose comprises flexible plastic tubing of about ⅜ inch to about ⅝ inch internal diameter. Mechanical disconnects are optionally provided for partially disassembling system 178. "Y" fittings 180 on each hose permit one hose to connect each pair of balloons. Each hose may be color-coded to aid the operator in properly connecting each hose to the correct balloon pair.

In one embodiment, illustrated in FIG. 2, the ECP system 22 and table 40 are further configured to facilitate transport of the system. ECP system 22 and table 40 may each have at least one wheel 30 to permit rolling of each component when the component is tilted onto wheels 30. Handles 34 may be provided for gripping and leverage when tilting. ECP system 22 and table 40 also have at least one leg 32 to prevent movement of the components without the use a brake.

To utilize one embodiment of the ECP system previously described, a patient is laid on table 40 and two right leg cuffs 42, two left leg cuffs 44, and buttock cuff 46 are placed on the patient. An off-the-shelf ECG monitor is connected to the patient to provide an ECG signal. ECP system 22 is then powered up using on/off power switch 24. The treatment duration for the patient set on timer switch 26. Start switch 28 is then pressed to start the treatment. The intervals between the detection of a QRS complex and the initialization of the first output or control signal from PLC 80 is determined by the average heart rate over the previous series of QRS complexes or over a previous period of time. By basing the delay interval of the first control signal on the R-to-R interval, a patient population with a greater range of resting heart rates may be treated. It is contemplated that patients with resting heart rates up to about ninety beats per minute (bpm) can undergo treatment, but patients with resting hearts rates up to about 110 bpm may be treated. The duration of the first output, the duration and intervals of the subsequent outputs originating from the detected QRS complexes are preset or calculated by the system. In one embodiment, the delay interval is 25% of the average of the last eight peak-to-peak intervals of squared ECG signal. The inflation pressures of bladders 64 are also preset by the system to a maximum of about 200 mm Hg. In the event of a power failure, ECP system 22 will stop operating and not restart unless start switch 28 is pressed. Air valves 58 will also revert to normally closed positions and vent bladders 64 during a power outage when no control signals are provided by PLC 80. To stop the treatment before the time ends, on/off power switch 24 is pressed. The time remaining for treatment on timer switch 26 does not change due to stops or power failures.

A signal from the ECG monitor is sent to ECP system 22 through ECG input connector 29. The signal goes to ECG timing board 92 where it is amplified and relayed to programmable logic controller 80. Programmable logic controller 80 sends a signal to air valves 58 controlling right leg cuff 42 and left leg cuff 44 placed on the lower thighs or upper posterior knees. Approximately forty milliseconds later, programmable logic controller 80 sends another signal to air valve 58 controlling right leg cuff 42 and left leg cuff 44 placed on the upper thighs or inguinal regions. After another approximately forty milliseconds delay, the programmable logic controller 80 sends a signal to two air valves 58 controlling buttock cuff 46 placed on the buttocks. The signals terminate generally at the same time after a fixed interval following the detection of the QRS complex in that cycle.

With the air assist provided from mini air compressor 96, the signals from PLC 80 opens air valves 58. The pressurized fluid from air compressor 50 passes through air tank 52. The fluid then passes through pressure regulator 54. The pressure is set at a limit of about 155 to about 240 mm Hg by pressure regulator 54. In one embodiment of the invention, the pressure is preset to 200 mm Hg. Pressure buildup over about 700 mm Hg is vented by pressure relief valve 56. When air valve 58 opens, it closes the exhaust port and allows pressurized fluid to inflate balloon 64. After a preset time of about 450 milliseconds from the start of lower thigh inflation, the signals from programmable logic controller 80 are stopped. When the signals stop, air valves 58 close at about the same time and vent the pressures in balloons 64. Valves 58 allow balloons 64 to inflate if there is power and signal from programmable logic controller 80. Any interruption of power will cause air valve 58 to close and exhaust balloons 64. The venting of balloons 64 is a fail-safe in case of power loss. This cycle is repeated until the treatment period finishes.

In a further embodiment of the invention, right leg cuffs 42, left leg cuffs 44, and buttock cuff 46 are placed on the patient. Right leg cuffs 42, left leg cuffs 44 and buttock cuff 46 are tightened by inserting the cuff end into buckle 122 and pulling the cuff end tight. Once tight, the cuff ends are pressed to fasten hook fastener 130 to loop fastener 132. Preferably, right leg cuffs 42, left leg cuffs 44, and buttock cuff 46 are tightened to give effective treatment. Use of buckle 122 and buckle roller 124 facilitates tightening of the cuffs by the operator. The buckle shield 126 reduces pinching of the patient's skin by buckle 122. Balloons 64 of right leg cuffs 42, left leg cuffs 44 and buttock cuff 46 are connected to balloon air lines 48. Balloon air lines 48 both inflate and deflate balloons 64. Balloon 64 is held in place on right leg cuff 42, left leg cuff 44 or buttock cuff 46 with hook fastener ring 112 and loop fastener 132. This allows balloon 64 to be independently replaced without having to replace right leg cuff 42, left leg cuff 44 or buttock cuff 46. Using hook fastener ring 112 and loop fastener 132 allows attachment of balloon 64 to the cuff without the use of cuff pockets. Balloon wall 110 can transfer the pressure to the patient without any reduced effect from added layers of material and result in more efficient treatment while using less pressure.

Alternatively, if cuffs that are adapted for disposability are desired, left leg cuff 150, right leg cuff 156 and buttock cuff 154 may be used. Cuffs 150, 154 and 156 are tightened in the same manner as previously described. The operator removes the adhesive protector from self-adhesive hook and loop fastener 146 and presses the portions of cuffs 150, 154 and 156 overlying self adhesive hook and loop fastener 146 to adhere fastener 146 to another portion of the cuff. Cuffs 150, 154 and 156 may be unfastened and refastened using the hook and loop fastening of self-adhesive hook and loop fastener 146. Vascular access to the femoral arteries and veins, or a vascular catheter already placed therein, are accessible through access openings in cuff material 144.

While embodiments of this invention have been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A compression system for external counterpulsation comprising:

at least three separate compression members for compressing the body of a patient, one of said compression members configured to be attached to a left thigh portion of a patient, one of said compression members configured to be attached to a right thigh portion of said patient; and a plurality of retention members adapted to hold said compression members against the body;

wherein a total surface area of the at least three separate compression members comprises no more than 240 square inches;

wherein the compression system comprises two compression members configured to be attached to the buttocks.

2. The system of claim 1, wherein said at least three separate compression members comprise inflatable bladders, and wherein an inflation pressure for each of said inflatable bladders is no more than 220 mm Hg.

3. The system of claim 1, wherein said compression members comprise electromechanical actuators.

4. The system of claim 1, wherein said retention members comprise cuffs.

5. The system of claim 1, wherein at least one said compression member and one said retention member are integrally formed.

6. The system of claim 1, wherein at least one said compression member and one said retention member comprise the same material.

7. The system of claim 1, comprising at least five inflatable compression members, one of said compression members being attached to a lower left thigh portion of the patient, one of said compression members being attached to an upper left thigh portion of the patient, one of said compression members being attached to a lower right thigh portion of the patient, one of said compression members being attached to an upper right thigh portion of the patient, and one of said compression members being attached to the buttocks portion of the patient.

8. The system of claim 1, wherein the system is configured to provided compression only to superior-posterior knee regions, the inguinal regions and buttocks, and no other parts of the body.

9. The system of claim 1, wherein the compression members comprise inflatable bladders, and the external counterpulsation system is configured to not decompress the inflatable bladders during a premature ventricular contraction.

10. A method for performing external counterpulsation, comprising:

providing an external counterpulsation system having a plurality of activateable compression members, an energy source for activating said compression members, a physiological sensor and a compression member controller;

attaching said compression members to a patient, said compression members comprising a first compression member located on a lower left thigh of a patient, a second compression member on an upper left thigh of a patient, a third compression member on a lower right thigh of a patient, a fourth compression member on an upper right thigh of a patient, and at least a fifth compression member on a buttocks portion of the patient;

sensing heart activity in said patient;

compressing said patient with said activateable compression members in synchrony with said heart activity;

wherein said compressing step comprises the compression member controller sending a first signal to the energy source to send air to the compression members on the lower left and right thighs after a first delay, the compression member controller sending a second signal to the energy source to send air to the compression members in the upper left and right thighs after a second delay of approximately 40 milliseconds, and the compression member controller sending a third signal to the energy source to send air to the at least one compression member on the buttocks portion after a third delay of approximately 40 milliseconds.

11. The method of claim 10, wherein said compression members each have a compression surface area of less than about 40 square inches and the total compression surface area of said compression members is less than about 240 square inches.

12. The method of claim 10, wherein said compressing step comprises temporarily occluding the femoral veins of said patient at about the inguinal ligament.

13. The method of claim 10, comprising performing external counterpulsation on a patient without compressing the lower limbs below the knee.

14. The method of claim 13, wherein external counterpulsation is performed without compressing the patient above the buttocks.

15. The method of claim 10, wherein the first delay is approximately 280 milliseconds.

16. The method of claim 10, wherein the first delay is based on the patient's heart rate.

17. The method of claim 10, wherein the first delay is an average peak to peak interval of the last eight QRS complexes of the patient.

18. The method of claim 10, wherein the first signal is terminated at approximately the same time the second signal is sent.

19. The method of claim 10, wherein the compression members comprise inflatable bladders, and the external counterpulsation system is configured to not decompress the inflatable bladders during a premature ventricular contraction.

20. A compression system for external counterpulsation comprising:

at least three separate compression members for compressing the body of a patient, one of said compression members configured to be attached to a left thigh portion of a patient, one of said compression members configured to be attached to a right thigh portion of said patient, and one of said compression members configured to be attached to a buttocks portion of said patient; and a plurality of retention members adapted to hold said compression members against the body;

wherein a total surface area of the at least three separate compression members comprises no more than 240 square inches;

wherein the compression member configured to be attached to the buttocks comprises an hour-glass shaped inflatable bladder.

* * * * *